United States Patent
Bechtel et al.

(10) Patent No.: US 9,103,793 B2
(45) Date of Patent: Aug. 11, 2015

(54) INTRINSIC RAMAN SPECTROSCOPY

(75) Inventors: Kate Bechtel, Somerville, MA (US);
Wei-Chuan Shih, Cambridge, MA (US);
Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1783 days.

(21) Appl. No.: 11/492,214

(22) Filed: Jul. 24, 2006

(65) Prior Publication Data
US 2007/0049809 A1 Mar. 1, 2007

Related U.S. Application Data

(60) Provisional application No. 60/701,839, filed on Jul. 22, 2005, provisional application No. 60/735,986, filed on Nov. 10, 2005.

(51) Int. Cl.
*A61B 5/1455* (2006.01)
*G01N 21/65* (2006.01)
*A61B 5/145* (2006.01)

(52) U.S. Cl.
CPC .............. *G01N 21/65* (2013.01); *A61B 5/1455* (2013.01); *A61B 5/14532* (2013.01); *A61B 5/14546* (2013.01); *A61B 2560/0223* (2013.01)

(58) Field of Classification Search
CPC .......................... A61B 5/1455; A61B 5/14532
USPC .................................................. 600/309–344
See application file for complete search history.

(56) References Cited

U.S. PATENT DOCUMENTS

| | | | |
|---|---|---|---|
| 5,452,723 A | 9/1995 | Wu et al. | |
| 5,481,113 A | 1/1996 | Dou et al. | |
| 5,615,673 A | 4/1997 | Berger et al. | |
| 5,754,289 A | 5/1998 | Ozaki et al. | |
| 5,828,450 A | 10/1998 | Dou et al. | |
| 5,842,995 A | 12/1998 | Mahadevan-Jansen et al. | |
| 6,044,285 A * | 3/2000 | Chaiken et al. | ............... 600/316 |
| 6,064,897 A | 5/2000 | Lindberg et al. | |
| 6,070,093 A | 5/2000 | Oosta et al. | |

(Continued)

FOREIGN PATENT DOCUMENTS

WO    WO 96/29925    10/1996
WO    WO 2004/105595    12/2004

OTHER PUBLICATIONS

Mobley et al., "Single-board computer based control system for a portable Raman device with integrated chemical identification," American Institute of Physics, Review of Scientific Instruments, vol. 75, No. 6, Jun. 2004.

(Continued)

*Primary Examiner* — Eric Winakur
*Assistant Examiner* — Marjan Fardanesh
(74) *Attorney, Agent, or Firm* — McCarter & English, LLP

(57) ABSTRACT

The present invention relates to systems and methods for the measurement of analytes such as glucose. Raman and reflectance spectroscopy are used to measure a volume, of material such as a blood sample or tissue within a subject and determine a concentration of a blood analyte based thereon. The present invention further relates to a calibration method, constrained regularization (CR), and demonstrates its use for analyzing spectra including, for example, the measurement glucose concentrations using transcutaneous Raman spectroscopy.

70 Claims, 16 Drawing Sheets

(56) References Cited

U.S. PATENT DOCUMENTS

| | | | |
|---|---|---|---|
| 6,167,290 | A | 12/2000 | Yang et al. |
| 6,181,957 | B1 | 1/2001 | Lambert et al. |
| 6,197,503 | B1 | 3/2001 | Vo-Dinh et al. |
| 6,377,828 | B1 | 4/2002 | Chaiken et al. |
| 6,424,850 | B1 | 7/2002 | Lambert et al. |
| 6,494,576 | B1 | 12/2002 | L'Esperance, Jr. |
| 6,522,903 | B1 | 2/2003 | Berman et al. |
| 6,560,478 | B1 | 5/2003 | Alfano et al. |
| 6,567,678 | B1 | 5/2003 | Oosta et al. |
| 6,574,501 | B2 | 6/2003 | Lambert et al. |
| 6,662,030 | B2 | 12/2003 | Khalil et al. |
| 6,690,966 | B1 | 2/2004 | Rava et al. |
| 6,721,582 | B2 | 4/2004 | Trepagnier et al. |
| 7,039,446 | B2 | 5/2006 | Ruchti et al. |
| 7,133,710 | B2 | 11/2006 | Acosta et al. |
| 7,505,128 | B2 | 3/2009 | Zribi et al. |
| 2003/0144582 | A1 | 7/2003 | Cohen et al. |
| 2003/0176777 | A1 | 9/2003 | Muller-Dethlefs |
| 2003/0191398 | A1 | 10/2003 | Motz et al. |
| 2003/0227628 | A1 | 12/2003 | Kreimer et al. |
| 2004/0019283 | A1* | 1/2004 | Lambert et al. ............... 600/476 |
| 2004/0039269 | A1 | 2/2004 | Ward et al. |
| 2005/0010090 | A1 | 1/2005 | Acosta et al. |
| 2005/0027176 | A1 | 2/2005 | Xie |
| 2005/0030657 | A1 | 2/2005 | Maier et al. |
| 2005/0043597 | A1 | 2/2005 | Xie |
| 2005/0090750 | A1 | 4/2005 | Ediger et al. |
| 2006/0063991 | A1 | 3/2006 | Yu et al. |
| 2006/0063992 | A1 | 3/2006 | Yu et al. |
| 2006/0063993 | A1 | 3/2006 | Yu et al. |
| 2006/0211926 | A1* | 9/2006 | Yu et al. ....................... 600/316 |
| 2006/0240401 | A1 | 10/2006 | Clarke et al. |
| 2008/0306363 | A1 | 12/2008 | Chaiken et al. |
| 2009/0073432 | A1 | 3/2009 | Jalali et al. |

OTHER PUBLICATIONS

Berger et al., "An Enhanced Algorithm for linear multivariate calibration," Analytical Chemistry, vol. 70, No. 3, Feb. 1, 1998.

Wentzell et al., "Maximum likelihood multivariate calibration," Analytical Chemistry, vol. 69, No. 13, Jul. 1, 1997.

Haaland et al., "New classical least-squares/partial least-squares hybrid algorithm for spectral analyses," Applied Spectroscopy, vol. 55, No. 1, 2001.

Koo, Tae-Woong, "Measurement of blood analytes in turbid biological tissue using near-infrared Raman spectroscopy," Massachusetts Institute of Technology, Aug. 2001.

* cited by examiner

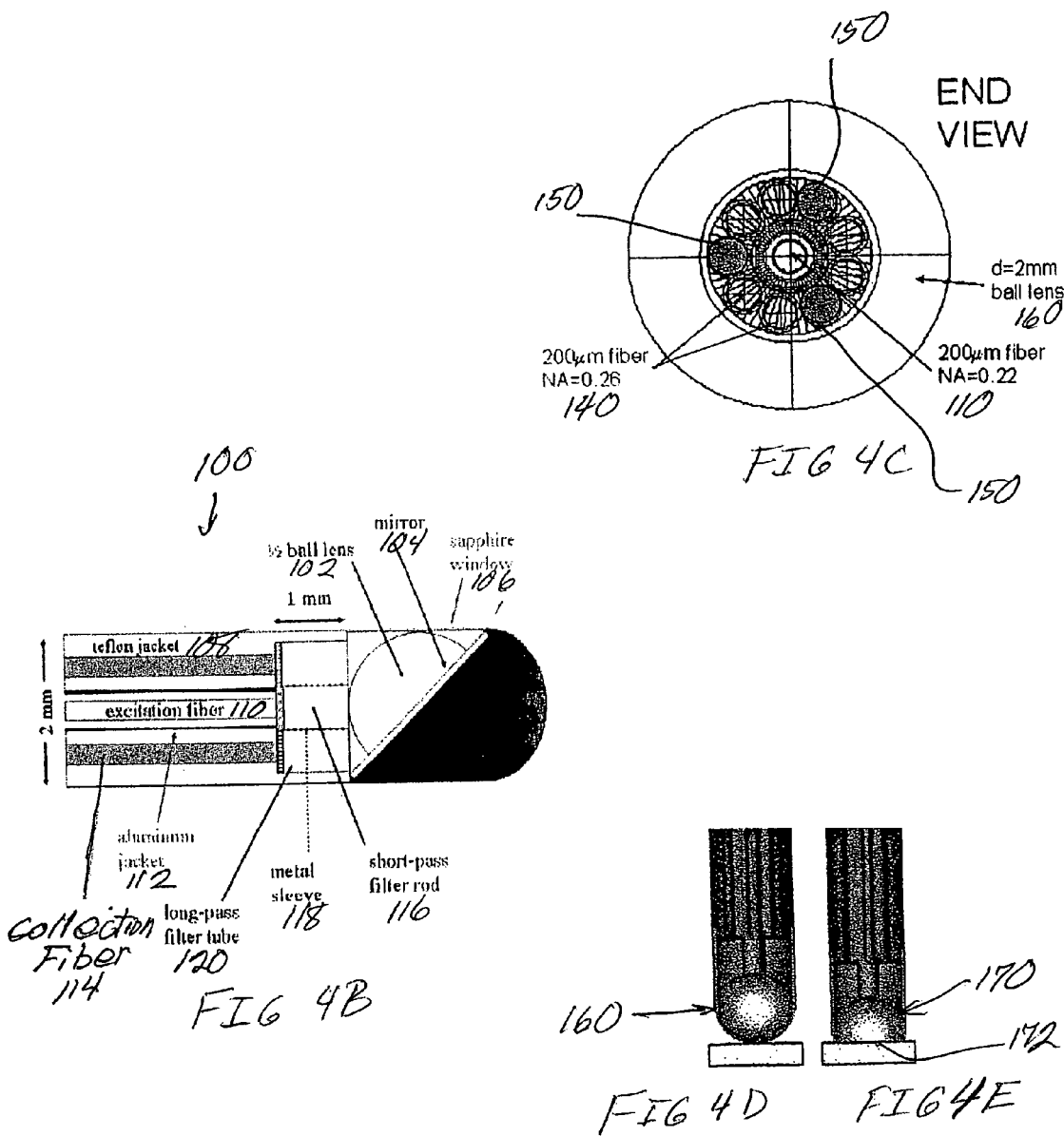

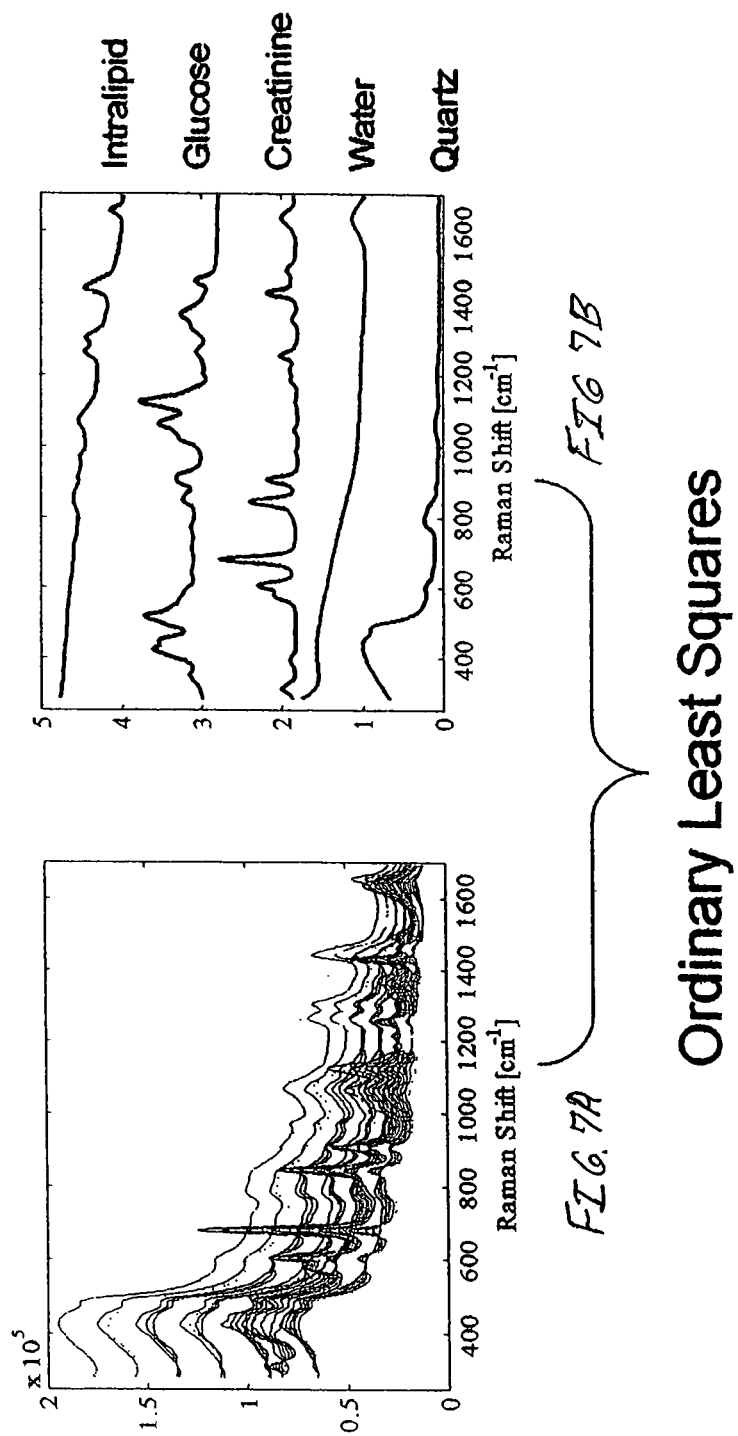

SEP = 1% = 6 mM, clear samples
SEP = 26% = 131 mM, turbid samples

SEP = 2% = 9 mM, clear samples
SEP = 23% = 129 mM, turbid samples

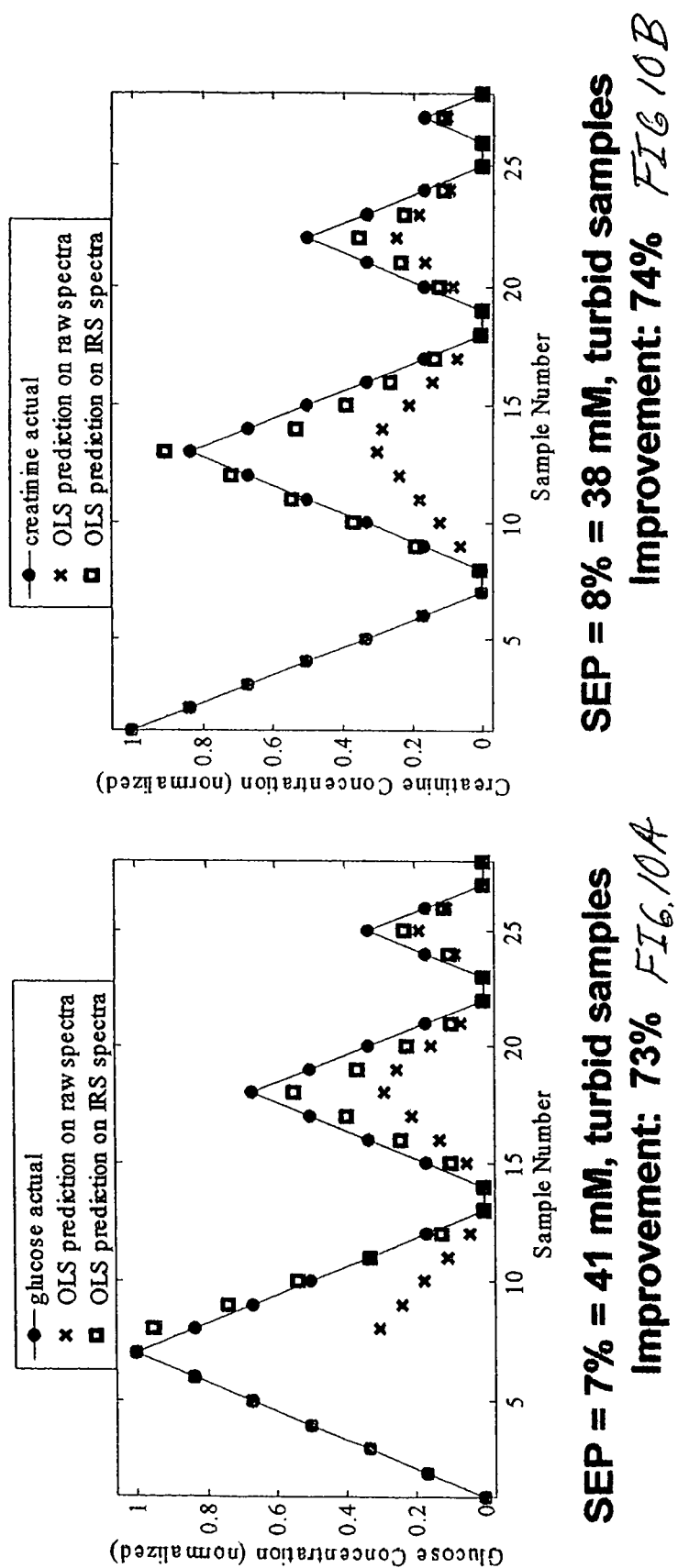

Providing a transformation by determining a regularized calibration vector that is a summation of a plurality of regularized and spectrally constrained components

Applying the transformation to a measured spectrum such as a Raman spectrum of blood glucose, by taking a product of the spectrum and the regularized calibration vector

Determining a concentration of an analyte such as blood glucose

FIG. 18B

INTRINSIC RAMAN SPECTROSCOPY

CROSS REFERENCE TO RELATED APPLICATIONS

This application claims the priority of U.S. Provisional Application No. 60/701,839 filed Jul. 22, 2005 and U.S. Provisional Application No. 60/735,986 filed Nov. 10, 2005. The entire contents of the above applications are being incorporated herein by reference.

BACKGROUND OF THE INVENTION

The development of non-invasive systems and methods for the transcutaneous measurement of blood analytes, such as glucose, remain important for the diagnosis and treatment of a variety of conditions. Conventional blood sampling methods are painful and have other undesirable features. However, none of the non-invasive methods being developed has demonstrated sufficient accuracy or reproducibility for clinical use. A major obstacle in achieving reproducible optical measurement such as Raman spectroscopy is the variation in optical properties (absorption and scattering) from measurement site to site, from subject to subject, and over time. Optical properties are important because the amount of absorption and scattering in a sample greatly influences the volume of tissue sampled by the excitation light and the magnitude of the collected Raman signal. A method to correct for this is necessary for the success because of the way calibration is performed. Reference concentrations obtained from a blood glucose or interstitial glucose measurement are used to correlate a given Raman spectrum with the concentration of glucose that spectrum should contain. Significant errors in calibration transfer are prone to occur if the number of glucose molecules sampled by the Raman instrument on day two is different than day one and yet the concentration of glucose molecules in the blood is the same. In other words, spectroscopic techniques such as Raman are sensitive to the number of glucose molecules sampled in the blood-tissue matrix, whereas the reference measurement provides the concentration (number÷volume) of glucose molecules in the blood or interstitial fluid.

To further improve optical measurements of blood analytes multivariate calibration has been used as an analytical technique for extracting analyte concentrations in complex chemical systems that exhibit linear response. Multivariate techniques are particularly well suited to analysis of spectral data, since information about all the analytes can be collected simultaneously at many wavelengths. Explicit calibration methods are often used when all of the constituent spectra can be individually measured or pre-calculated. Examples are ordinary least squares (OLS) and classical least squares (CLS). When individual spectra are not all known, implicit modeling techniques are often adapted. Principle component regression (PCR) and partial least squares (PLS) are two frequently used methods in this category. In either case, the goal of multivariate calibration is to obtain a spectrum of regression coefficients, b, such that an analyte's concentration, c, can be accurately predicted by taking the scalar product of b with a spectrum, s:

$$c = s^T \cdot b \qquad (1)$$

(Lowercase boldface type denotes a column vector, uppercase boldface type a matrix; and the superscript $^T$ denotes transpose.) The regression vector, b, is unique in an ideal noise-free linear system without constituent correlations, and the goal of both implicit and explicit schemes is to find an accurate approximation to b for the system of interest.

Explicit and implicit methods have their own advantages and limitations. Explicit methods provide transparent models with easily interpretable results. However, they require high quality spectra and accurate concentration measurements of each of the constituent analytes (or equivalent information), which may be difficult to obtain, particularly in in vivo applications. Implicit methods require only high quality calibration spectra and accurate concentration measurements of the analyte of interest, (the "calibration data"), greatly facilitating system design. However, unlike explicit methods, the performance of implicit methods can both be simply judged by conventional statistical measures such as goodness of fit. Spurious effects such as system drift and co-variations among constituents can be incorrectly interpreted as legitimate correlations. Furthermore, implicit methods such as PCR and PLS lack the ability to incorporate information about the system or analytes, in addition to the calibration data, into b. Such prior information can, in principle, improve measurement accuracy. In particular, in many cases it is desirable to use prior spectral information about the constituent analytes. Such information generally helps stabilize and enhance deconvolution, classification and/or inversion algorithms. In multivariate calibration, methods combining explicit and implicit modeling, such as hybrid linear analysis (HLA), achieve the same goal by removing the contribution of the known analyte spectrum of interest from the sample spectra. Thus, there remains a need for further improvements in systems and methods for the non-invasive measurement of blood analytes.

SUMMARY OF THE INVENTION

The present invention relates to measurements of blood analytes such as glucose concentration in human or animal subjects. Systems and methods can include non-invasive transcutaneous measurements of glucose concentration using Raman and reflectance spectroscopy. Alternatively, a probe can be for the internal measurement of blood analytes, or in another embodiment systems and methods can be used for the measurement of blood or tissue samples removed from the body of a subject.

A preferred embodiment includes a system for performing measurements in accordance with the invention that has a light source for Raman excitation and reflectance measurements. In a further embodiment, a first light source is used for the Raman measurements and a second light source is used for reflectance measurements. Light delivery and collection systems can deliver light onto the surface of the skin of the subject and collect light returning therefrom. A detector records the collected Raman and reflectance data and delivers the data to a processor for determination of the sampling volume within the tissue, provides a corrected Raman spectrum and a concentration level for the analyte of interest. A preferred embodiment for the first light source can be a laser emitting in the infrared range of 750 nm to 1200 nm and can comprise a diode laser emitting at 830 nm, for example. The second light source can be a white light source such as a tungsten halogen lamp.

Preferred methods for processing the acquired data can include a partial least squares (PLS) analysis. PLS with leave-one-out cross validation can be carried out on data from each individual so that errors from site-to-site and individual differences are reduced. The most significant cause of calibration error can be the substantial temporal changes in the measured Raman spectra that are observed. These temporal changes are not believed to be a result of instrumental drift or systematic error and as such are not isolated to a particular instrument. The large magnitudes of such changes also preclude them from being manifestations of blood glucose concentration variation.

In order to equate the measurement of blood glucose molecules, for example, it is preferable that two conditions be met: (1) that the sampling volume be constant or corrected for and (2) the percentage of glucose-containing fluid within this volume be constant. The latter condition may be met by ensuring the same area is sampled, the pressure on the surrounding tissue is similar, and the subject maintains a similar hydration level from day to day.

In near-infrared absorption experiments, the common solution is to scale the spectra to the prominent water absorption peak, the assumption being that glucose molecules are water-soluble and therefore water serves as an internal standard. However, the effects of sample dehydration in the upper tissue layers during the course of the measurement may limit the usefulness of water as an internal standard. The region of interest (300 1800 $cm^{-1}$) for biological Raman spectroscopy does not have a strong contribution from water. The strongest water band, at 1640 $cm^{-1}$, is overwhelmed by the protein amide band occurring at the same position. Further, adjusting the spectra to the height of a particular peak does not account for spectral distortions that may occur as a result of temperature variations or the presence of an absorption feature.

A preferred embodiment of the invention addresses these temporal variations using processing that can include determination of a ratio of the Raman data with the diffuse reflectance (DR) data to provide corrected spectral data and thereby remove distortions caused by the turbidity of the tissue being measured. This ratio produces an intrinsic Raman spectrum (IRS) that can help reduce temporal changes in the measurement. Additionally, by determining the sampling volume of the tissue being measured, by dividing the number of glucose molecules measured using Raman excitation by the sampling volume, a quantitative measurement of blood glucose concentration is obtained.

The present invention uses reference information with calibration data in an implicit representation. Starting with the inverse mixture model as the forward problem, the inverse problem has a solution b. Instabilities associated with the inversion process are removed using a technique known as regularization, and prior information is included using a spectral constraint. This method is referred to herein as constrained regularization (CR).

In a preferred embodiment, human data with elevated glucose levels, obtained via transcutaneous Raman spectroscopy can be analyzed using this method. With CR, both the standard error obtained using leave-one-out cross validation (SEV) and the standard error of prediction (SPE) improve compared to results obtained using PLS. CR analysis of blood analytes are also applicable to multivariate techniques that employ near infrared spectroscopy, as well as Raman spectroscopy.

An additional factor that greatly affects the performance of the calibration algorithm is the accuracy of the reference measurements. Previous studies have used the blood plasma glucose concentrations collected at five minute intervals as the reference concentrations in building the calibration algorithm. However, if the glucose Raman spectra primarily originates from interstitial fluid, then the differences between interstitial fluid and plasma glucose concentrations can contribute to the error in the measurements.

To address the issues of sampling volume correction and the relative roles of interstitial fluid and plasma glucose, preferred embodiments of the present invention seek to address difficulties with calibration transfer which is impeded by variations in sampling volume as a result of differences in tissue scattering and absorption. By correcting for the sampling volume with diffuse reflectance spectroscopy, the system is able to apply a calibration obtained at one time in one individual to that same individual at another time. Additionally, it is noted that the glucose in the interstitial fluid provides a substantial contribution to the glucose Raman signal, and the lag time between plasma and interstitial glucose concentrations gives rise to measurement error. Therefore, the information obtained from interstitial fluid glucose measurements in combination with those from plasma glucose can be used to provide a calibration with reduced error, compared to a calibration derived from plasma glucose measurements alone.

Consequently the combined use of intrinsic Raman spectroscopy to correct for sampling volume variations and interstitial fluid glucose measurements improves noninvasive analysis and can provide successful calibration transfer.

DESCRIPTION OF THE DRAWINGS

FIG. 4B illustrates a side looking fiber optic probe.

FIG. 4C shows a distal end of a fiber optic probe for use within a human or animal body.

FIG. 4D illustrates a forward looking fiber optic probe or catheter with a ball lens.

FIG. 4E illustrates a forward looking probe or catheter with a half ball lens.

FIGS. 7A and 7B show Raman spectra and components of the tissue phantom, respectively.

FIGS. 10A and 10B show plots with corrected Raman data for glucose and creatinine, respectively.

FIG. 18B illustrates a process for using constrained regularization to calculate a spectrum.

DETAILED DESCRIPTION OF THE INVENTION

Preferred embodiments of the present invention relate to the use of Raman spectroscopy for the measurement of blood analytes. Systems and methods used in conjunction with preferred embodiments include those described in U.S. Pat. No. 5,615,673 and in U.S. Applications PCT/US96/04136, 60/675,252 filed on Apr. 27, 2005, 60/701,839 filed on Jul. 22, 2005, 60/702,248 filed on Jul. 25, 2005, and Ser. No. 11/412,418 filed Apr. 27, 2006 this patent and these applications being incorporated by reference into the present application in their entirety.

Figure 1A:
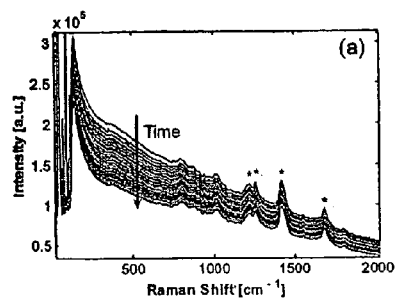
FIG. 1A shows a Raman signal from human forearm obtained with a Kaiser PhAT probe system at 785 nm over the course of 110 minutes (each trace is collected in 1.5 minutes).
Figure 1B:
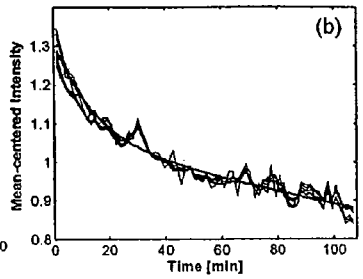
FIG. 1B shows mean-centered intensity of several different pixels across the spectral region as a function of time. The fit in red is a double exponential function.
Figure 1C:
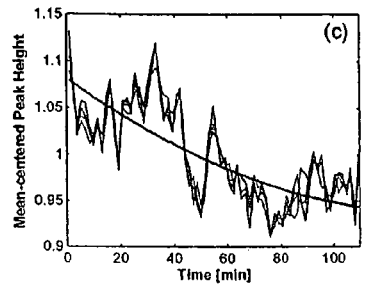
FIG. 1C shows mean-centered peak heights of the four asterisked Raman peaks in (FIG. 1A) as a function of time, the fit in red is a $2^{nd}$ order polynomial to guide the eye, but no particular function is known to fit this decay.

FIG. 1 depicts the signal obtained from a human forearm as observed with a commercial Kaiser PHAT probe Raman system with 785 nm excitation. The background signal, after spectral correction for the combined response of the grating and the CCD. Each trace is obtained with a 1.5 minute collection time and the overall signal level is seen to decrease over the course of the nearly 2 hour measurement. The intensity decays across the spectral region are shown in FIG. 1B. The fit, shown in red, is a double-exponential function. The background decay in Raman experiments has been observed to be well fit with a double exponential function. The peak heights of the four asterisked Raman peaks in FIG. 1A are plotted as a function of time in FIG. 1C. The peak heights are determined by a linear interpolation of the baseline under the peak. The fit, shown in red, is a $2^{nd}$ order polynomial although an exponential function could also have been used. The peak height data are noisy owing to the difficulty in extracting the background without modifying the peak height and because of likely sampling effects such as movement and blood flow. However, it is apparent that the Raman signal is changing over time. The overall decrease in Raman signal has been observed to be on the order of 7-15% over the course of 2-3 hours for different human subjects.

The downward trend in Raman peak heights as a function of time can be a result of laser-tissue interactions such as local heating-induced changes in the scattering properties of the sample, sample dehydration, heating-induced changes in the water absorption coefficient, etc. These variations, although unrelated to glucose levels, can be recognized as a legitimate correlation by the multivariate calibration algorithm and consequently impair the calibration results. To demonstrate how detrimental such spurious correlations can be to accurate prediction, a 10-component representation can be used to perform numerical simulations. For each calibration set, 25 spectral samples are formed with the pattern of glucose concentration variation designed to mimic an oral glucose tolerance test and other 9 interfering components (actin, cholesterol, collagen I, collagen III, water, hemoglobin, keratin, phosphatidylcholine and triolein) according to their magnitude in our in vivo background-removed skin Raman spectra. Within the 2 to 3 hour time period these 25 spectra are designed to simulate, the glucose concentration starts at ~90 mg/dL, rises linearly to ~220 mg/dL, and falls back to ~90 mg/dL. To examine the effects of a decreasing overall Raman signal level, a temporal exponential decay is superimposed onto the time-sequenced Raman spectra. The pattern of the exponential decay is controlled by one parameter: the peak intensity ratio between the last and the first spectral sample.

Figure 2:
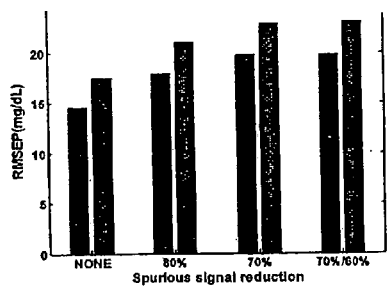
FIG. 2 shows simulation results of prediction error for various superimposed temporal decays: none, single exponential decay 80%, 70% and double exponential decay 70%/60%. For each temporal decay, two different signal-to-noise ratios were considered.

The representation considers all components experiencing the same overall signal decay, imitating a possible inner-filter effect. This examines single-exponential decay profiles towards 80% and 70% as well as a double-exponential decay profile towards 70%/60% for two different signal-to-noise ratios. FIG. 2 displays the results, which suggest that the error inflation is roughly linear with the amount of signal decay. For example, an exponential decay that decreases towards 80% of its initial peak height gives rise to 20% more error in prediction. It is emphasized again that such a decrease does not exactly follow the pattern of the glucose concentration variation; however its existence impairs the prediction accuracy due to the possibility of chance correlation to glucose.

This illustrates that even if the background signal, which itself is decreasing, can be completely removed from the spectrum without influencing the Raman peaks, a condition that is not guaranteed and will be discussed below. The non-glucose related changes in Raman peak intensity must be addressed. Because the laser power is not fluctuating by a significant amount, a provision that is ensured in the system by measuring the power with a beam splitter and photodetector during measurements, the only likely mechanism that can lead to a change in Raman signal level is optical property (absorption and scattering) changes of the sample.

Thus the present invention relates to the use of quantitative or intrinsic Raman spectroscopy, a technique to remove turbidity-induced spectral distortions to provide transcutaneous measurements of blood glucose and other blood analytes. The turbidity-free Raman spectra can originate from different sampling volumes, depending on the site and on the individual, and therefore may incorporate different amounts of glucose molecules. This is possible because human skin is a layered structure with glucose distributed in a highly non-uniform fashion. The relative thickness of each layered structure varies from site to site on an individual and from individual to individual.

A method to determine the sampling volume during a given Raman measurement would thus be useful. Reference concentrations obtained from a blood measurement (finger stick) can be used to correlate a given Raman spectrum with the concentration of glucose that spectrum contains. Significant errors in calibration are prone to occur if different individuals, or the same individual on a different day, who have the same level of glucose in their bloodstream as determined by a clinical instrument, have sufficiently different skin morphology such that the actual number of glucose molecules sampled by the Raman instrument is not the same. In other words, spectroscopic techniques such as Raman measurements are sensitive to the number of glucose molecules sampled in the blood-tissue matrix whereas the reference measurement provides the concentration (number divided by volume) of glucose molecules in the blood. In order to equate these measurements, it is preferable that two conditions be met: (1) the concentration of glucose in the combined interstitial fluid and blood capillaries be within a constant of proportionality to that in venous blood. This has been shown to be true, albeit the glucose concentration in interstitial fluid lags behind that in the blood by about 4-10 minutes, (2) the volume of these glucose-containing regions that are sampled in a given measurement can be determined.

In noninvasive measurements using near-infrared absorption spectroscopy, the latter condition is met by scaling spectra to the prominent water peak; the assumption being that glucose molecules are water-soluble and therefore water serves as an internal standard. It is unclear what effect sample dehydration in the upper tissue layers over the course of the measurement has on this method. Regardless, the Raman spectrum of tissue in the region of interest for many molecules (300-1800 $cm^{-1}$) does not have this option because the water band at 1640 $cm^{-1}$ is overlapped by the amide band.

Additionally, owing to the spatially heterogeneous distribution of glucose in the blood-tissue matrix, collecting Raman light from the entire 3D sampling volume of the excitation laser inevitably includes a large amount of undesired constituent Raman signatures, such as those of keratin and collagen. These Raman signatures not only generate extra counts of shot noise, but also interfere with the subsequent data analysis and compromise the overall performance.

The optical properties of a biological material or tissue are known to be affected by laser irradiation, typically as a result of laser heating. Much of the emphasis has been placed on large-scale temperature changes that result in tissue denaturation or coagulation. These changes are typically irreversible and occur at temperatures above 50 degrees Celsius. Smaller, reversible changes of optical properties occur at lower temperatures and signify effects ranging from thermal lensing (gradient in the index of refraction caused by localized heating) to thermal expansion of tissue. Additionally, the absorption coefficient of water has been shown to be highly dependent on temperature. Of the variety of thermo-optically induced scattering phenomena, two are known to have the effect of decreasing the diffuse reflectance (DR) of the tissue sample: changes in shape or size of scatterers resulting in a decrease of the reduced scattering coefficient ($\mu_s'$) and local dehydration that may increase the anisotropy of the cells towards forward scattering. The present invention utilizes the effects that lead to a reduction in diffuse reflectance because of the observed decreasing trend in Raman signal level. Diffusely reflected light is that which has undergone numerous elastic scattering events before escaping the tissue and thereby provides a metric for the amount of tissue absorption and scattering. The optical properties of a given sample can therefore be measured in situ by diffuse reflectance spectroscopy (DRS).

The present invention thus corrects not only for spectral distortions due to dispersions of endogenous absorbers and scatterers, but also for the changes in these properties over time and across samples. Hence, a continuous measurement of the DR can be used to offset any bulk optical property changes over the course of a Raman spectroscopy measurement.

Apart from the dynamic variations due to optical property changes upon laser-tissue interaction, existing differences across measuring sites or persons, for instance, as a result of slight variations in skin layer thickness, can limit the performance of a multiple-day or a multiple-sample measurement. To this end, a method to determine the volume of glucose-containing regions that are sampled in each measurement can be generated employing analytical models.

In the photon migration picture for light propagation in turbid media, diffuse reflectance can be characterized by three parameters: absorption coefficient ($\mu_a$), scattering coefficient ($\mu_s$), and scattering anisotropy (g). Extraction of these parameters from the DR spectra has been demonstrated. The present invention uses a light delivery and collection system in the wavelength range of interest, i.e., 830-1000 nm.

Further, with an efficient Monte Carlo method the effects of the layered structure of skin on its Raman spectrum is analyzed. Because most Raman scatterers have a specific spatial distribution in skin, such as keratin in the epidermis, collagen in the dermis, etc., a single homogeneous layer model does not fully represent the sample. A method has been developed for a two-layer structure in the spectroscopic diagnosis of precancerous cervical tissue using fluorescence spectroscopy.

As a starting point, note that human forearm skin can be represented as a two-layer structure composed of epidermis (including stratum corneum) and dermis, with homogeneity assumed within each individual layer. Such a distinction is made because epidermis is abundant in keratin and lacks glucose whereas dermis is rich in collagen (type 1) and contains interstitial as well as capillary glucose. Because keratin and collagen have such distinctive spatial distributions, information can be obtained about the thicknesses of the epidermis and dermis by comparing the relative magnitude of keratin and collagen Raman signals. This is dependent upon knowledge of the Raman scattering cross sections for keratin and collagen. Analytical models, using DRS and IRS, allow inversion and estimation of optical properties of each individual layer. Such estimates enable determinations of the exact sampling volume and to use it for calibrating the reference glucose concentration. In other words, by knowing the exact sampling volume and its coverage of various skin morphological structures, the method can estimate how much of the glucose-containing region (dermis in the two-layer model) is sampled. Note that this scaling value can differ from site to site and from person to person. Multiplication between the estimated glucose-specific sampling volume and the reference glucose concentration results in the number of glucose molecules actually sampled, which can be used in calibrating the Raman spectra. Using this calibration algorithm, the number of glucose molecules measured by Raman measurement can be divided by the sampling volume to obtain the blood glucose concentration.

Measurements can also be conducted on tissue phantoms with layered structures of known concentrations of Raman scatterers to demonstrate the efficacy of this technique. The combined use of Raman spectroscopy and DRS offer a method to correct for skin composition diversity.

Figure 3:
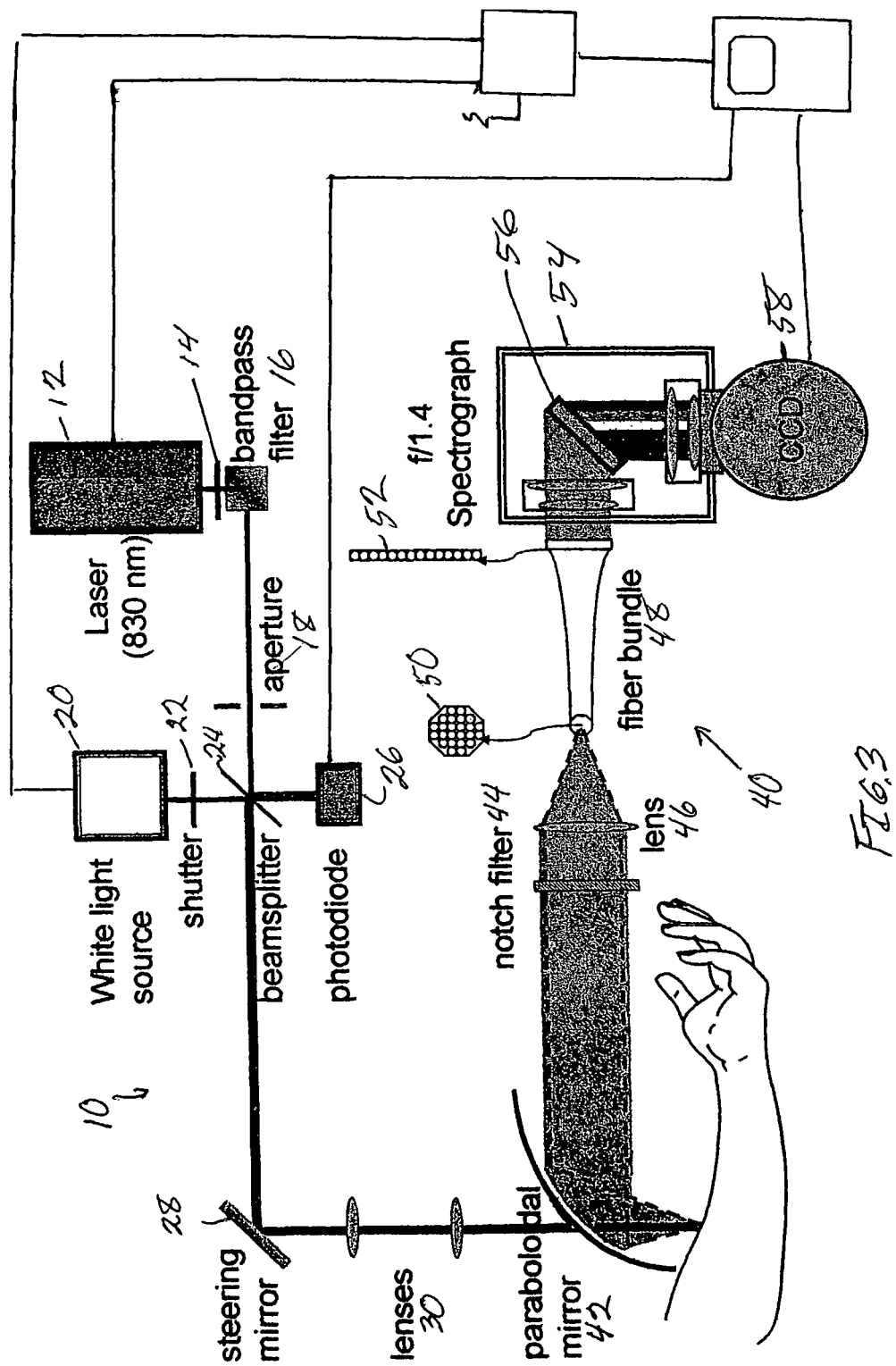
FIG. 3 illustrates a preferred embodiment of a system for obtaining Raman and reflectance data in accordance with the invention.

For measurements involving the simultaneous measurement of DR and Raman spectra, a bimodal instrument is required. The light delivery system 10 can employ a laser 12 emitting a narrowband pulse and a white light source 20 emitting a broadband signal and the collection system 40 can include the collection optics 42, 44, 46, 48, spectrometer 54, and CCD detector 58. FIG. 3 is an illustration of a preferred embodiment of the invention. Fiber bundle 48 collects over an area 50 and converts this area into a linear array 52 for coupling to the spectrograph dispersing element 56. A controller can be used to actuate the light sources. The controller an be used to actuate a shutter device.

As the embodiment uses two different excitation sources while retaining a single spectrometer, laser excitation of the sample and white light excitation of the sample must alternate. Shutters 14 and 22 can control coupling of light to beamsplitter 24, steering mirror 28 and lens 30. The duration and the frequency of the application of each excitation source can be used to correct for optical property changes while still obtaining high signal-to-noise Raman spectra. The light from both sources is directed on the same path to ensure that the excitation spot on the tissue is equivalent for both the laser and the white light source. Furthermore, the tungsten halogen lamp can be appropriately filtered such that light within the wavelength range of 830-1000 nm is transmitted. The out-of-range light is excluded to reduce stray light inside the spectrometer and possible heating of the tissue.

In the Raman mode of operation, a bandpass filter 16 that passes only 830 nm (6 nm FWHM) is necessary. A photodiode 26 monitors light source 12, 20 output for stability.

This system allows for the collection of DR from the same sample and under the same conditions that Raman spectra are acquired. The acquisition of DR enables the correction of the Raman spectra for time-dependent changes in optical properties of the sample and for differences in sampling volume.

Figure 4A:
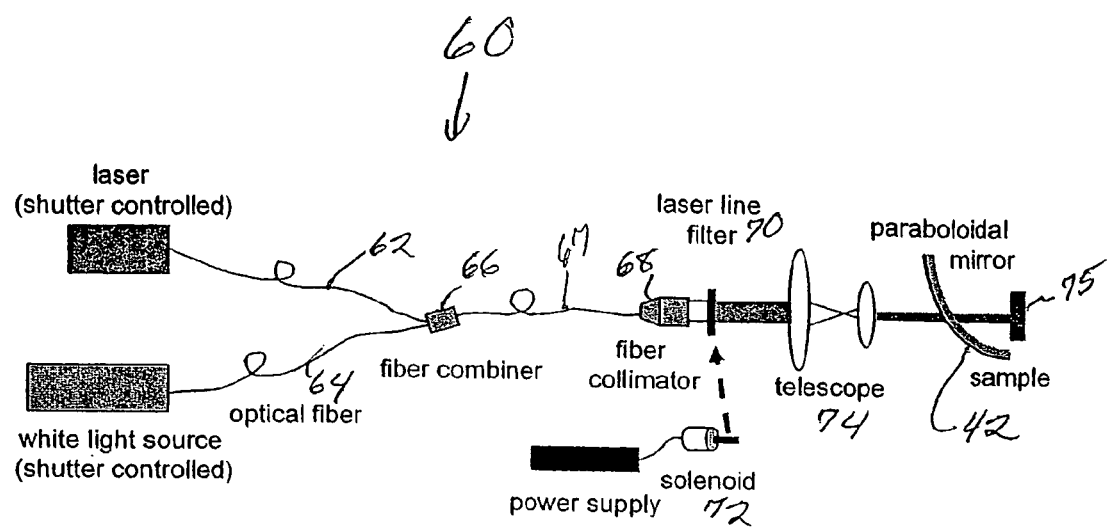
FIG. 4A shows another preferred embodiment of a light delivery system in accordance with the invention.

Another preferred embodiment of the light delivery system is illustrated in FIG. 4A. In this embodiment, optical fibers 62, 64 couple the two light sources through a fiber combiner 66 into a single optical fiber 67. A fiber collimator 68 than directs the light through a switched laser line filter 70, a telescopic lens 74 and a paraboloidal mirror 42 onto the patient or sample 75. This filter 90 must be removed in the DRS mode of operation to allow light in the described wavelength range to pass unobstructed. Thus, the laser line filter can be mounted on a software-controlled solenoid 92 synchronized with mode switching.

Another preferred embodiment can employ a fiber optic probe or catheter for use within body cavities, lumens, arteries, the heart, gastrointestinal tract, etc. to measure body tissue or fluids to determine the presence and/or concentration of analytes and to diagnose disease or other abnormalities.

The distal end of such a probe 100 can have a central excitation optical fiber 110 that is surrounded by aluminum jacket 112 as shown in FIG. 4B. The proximal end of the excitation fiber can be coupled to either one or two light sources as described herein. This particular embodiment is 2 mm in diameter, however, the device can have diameters of 1-3 mm for use in the arterial system or larger diameters for other body cavities. Outer wall or jacket 108 surrounds the flexible portion of the catheter 100.

The fiber 110 is filtered by a short pass filter rod 116 at the distal end which is surrounded by metal sleeve 118. The filter 116 couples the excitation pulse to a half ball lens 102, reflected off of mirror 104 and through sapphire window 106. The light returning from the tissue is collected along a path through window 106, reflected at 104, transmitted through lens 102 and collected by collection fibers 114. An end cross sectional view of the fibers is shown in FIG. 4C. The ball lens 160 covers the distal end with the central excitation fiber 110 (200 μm fiber with NA=0.22) surrounded by three pairs of collection fibers 140 used to collect Raman spectra. Each pair of the Raman fibers is separated by a collection fiber 150 (200 μm fiber with NA=0.26) that is used to collect a reflectance spectrum. The filter 120 (such as a long pass filter tube) is selected to transmit the desired collection spectrum which can be different depending on the Raman or reflectance spectrum being collected by a particular fiber.

In FIG. 4D a forward looking ball lens 160 is used. A forward looking catheter system employing a half ball lens system 170 as shown in FIG. 4E can provide a larger contact surface 172 at the distal end of the device.

Figure 5:
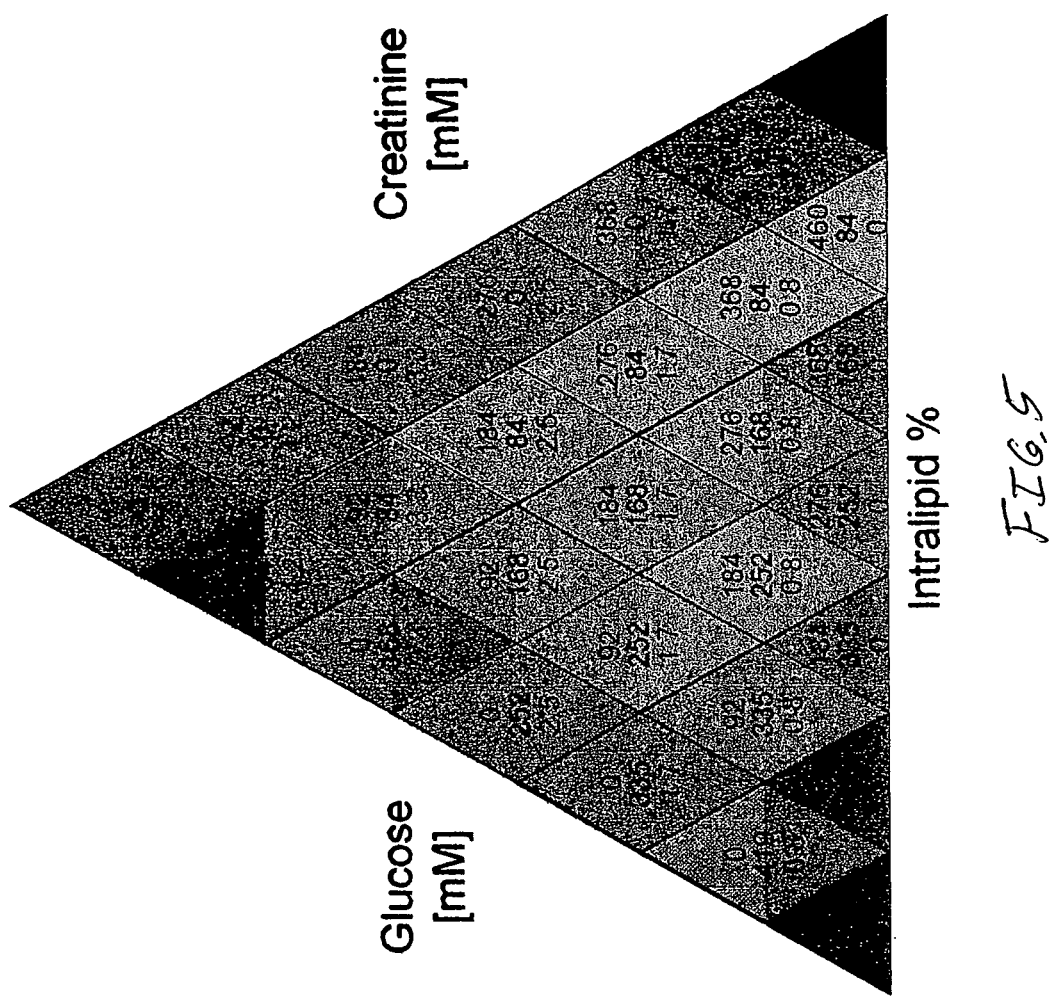
FIG. 5 shows a tissue phantom for use in conjunction with a preferred embodiment of the invention.
Figure 6:
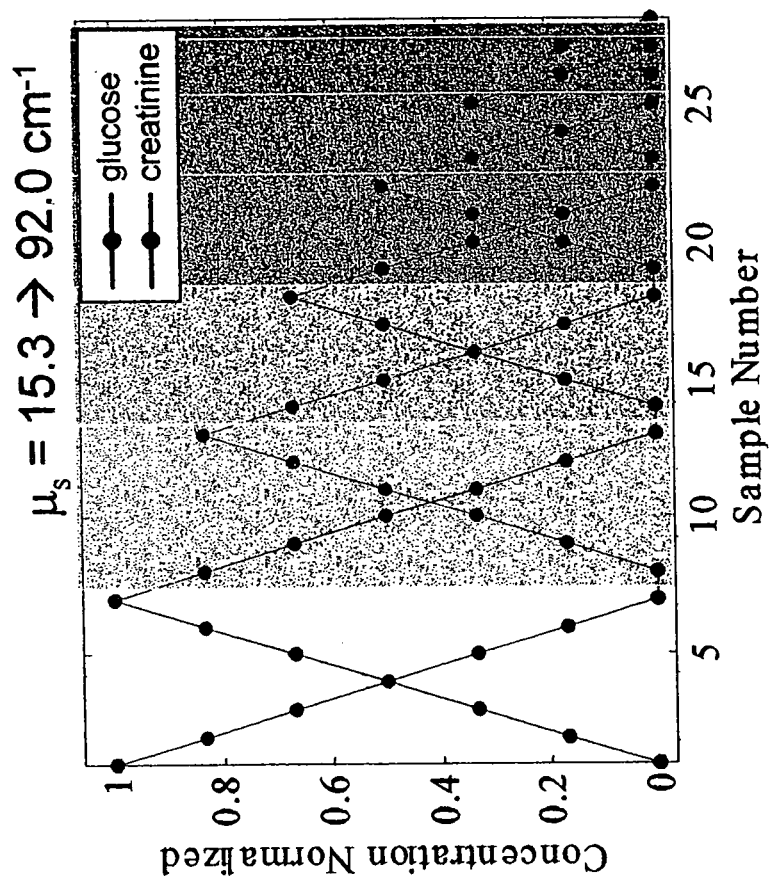
FIG. 6 shows a tissue phantom concentration profile.

FIG. 5 is a tissue phantom having the indicated distributions of glucose, creatinine and intralipid. Such a phantom can be used for calibration measurements. FIG. 6 shows the phantom concentration profile for the indicated components.

Figure 8B:
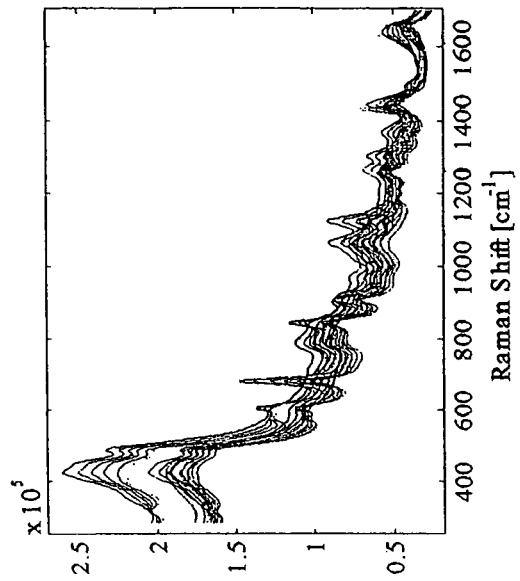
FIGS. 8A and 8B show diffuse reflectance and correct Raman spectra, respectively.
Figure 8A:
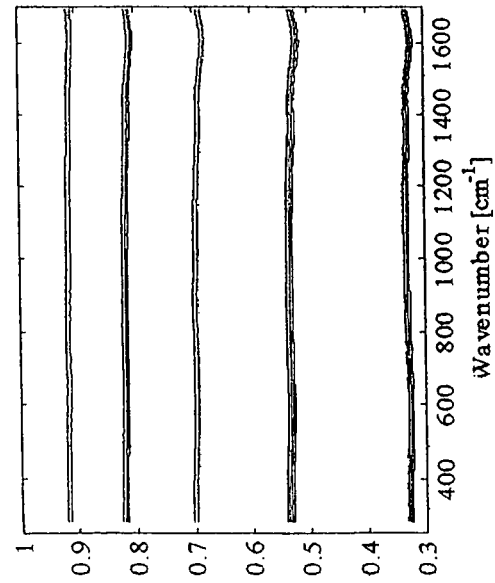

The Raman spectra of the phantom is shown in FIG. 7A with the individual components shown in FIG. 7B. The diffuse reflectance spectra (DRS) are shown in FIG. 8A and the intrinsic Raman spectra obtained from the measured Raman (FIG. 7A) and DRS are shown in FIG. 8B.

Figure 9B:
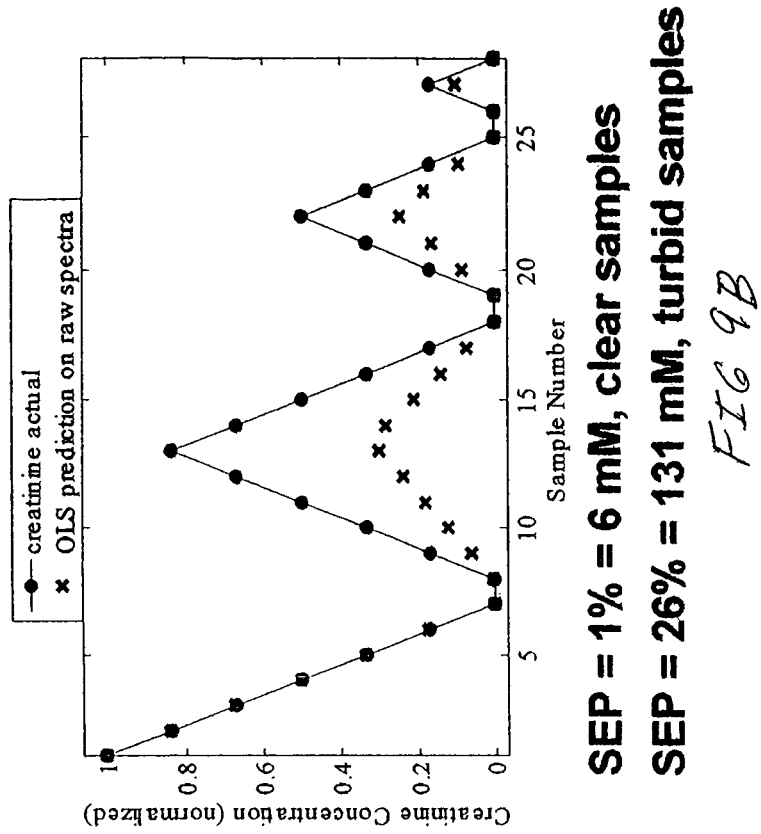
FIGS. 9A and 9B show plots of spectra for glucose and creatinine, respectively, using ordinary least squares.
Figure 9A:
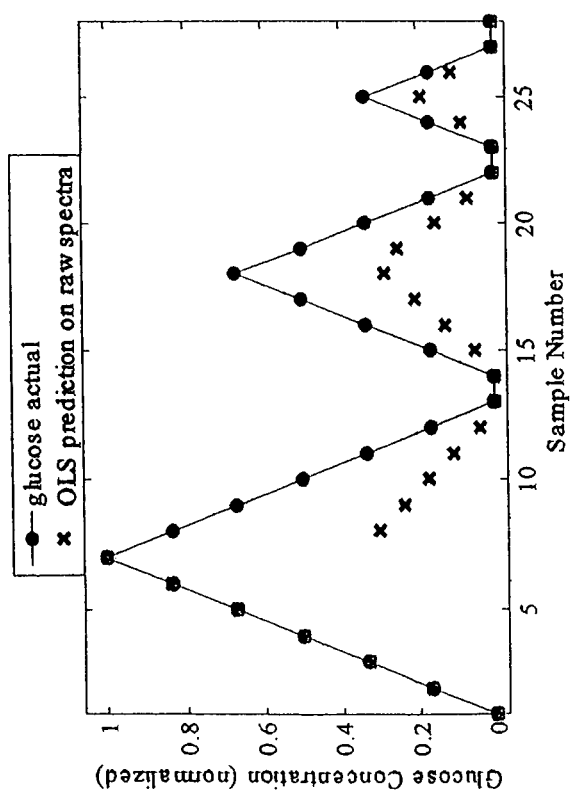

In FIG. 9A the actual glucose concentration is plotted for comparison with ordinary least squares analysis of the measured Raman spectrum. The comparative plot for creatinine is shown in FIG. 9B.

FIGS. 10A and 10B illustrate the improvement in measured data using an ordinary least squares analysis for the intrinsic Raman spectra. Using the intrinsic Raman spectra improvements of 73% and 74% were observed in the glucose and creatinine measurements, respectively.

Figure 11A:
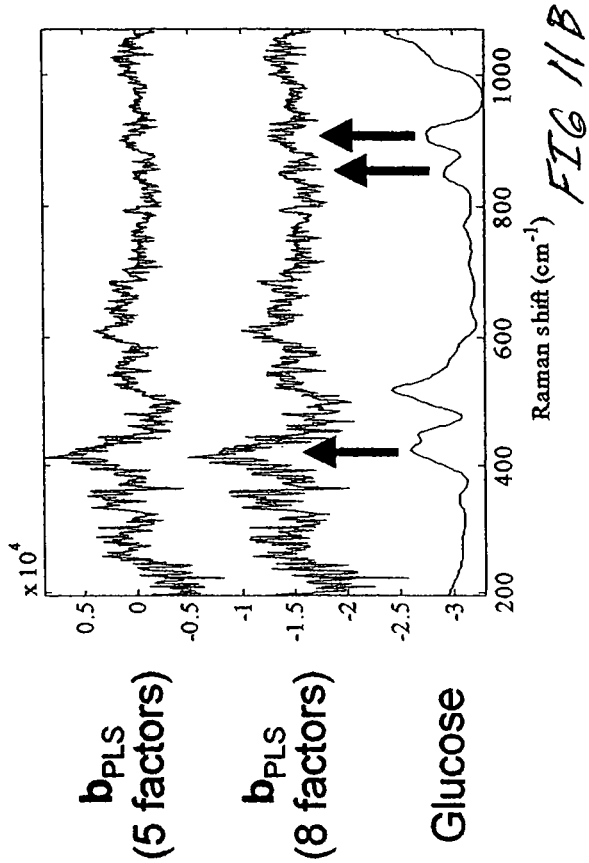
FIGS. 11A and 11B show Raman and corrected Raman data, respectively, for glucose using a partial least squares analysis.
Figure 11B:
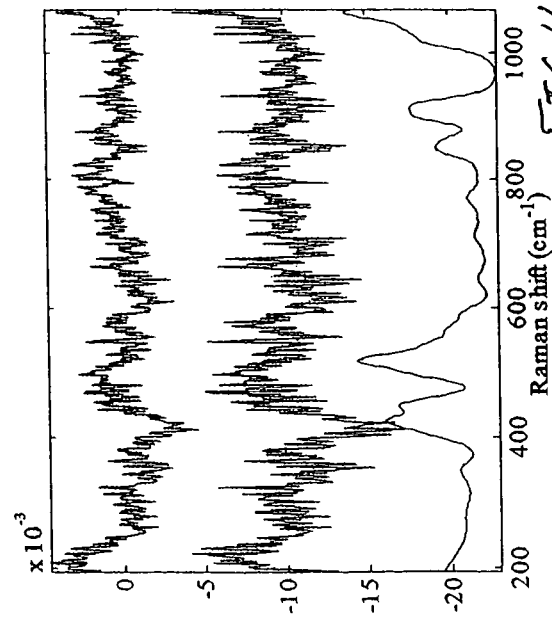

FIGS. 11A and 11B show the collected Raman spectra for glucose and the corrected IRS spectra, respectively, using a partial least squares multivariate calibration. The regression vector $b_{PLS}$ is described in greater detail hereinafter and in U.S. Application No. 60/701,839 filed on Jul. 22, 2005, the entire contents of which is incorporated herein by reference. The IRS spectrum has a clear correlation with the glucose peaks at the bottom of both spectra.

For applications in which $\mu_a$ and $\mu_s$ are relatively constant over the collected wavelength range, the following embodiment of the invention relates to a simple and effective correction for changes in sampling volume that does not require an additional light source or detector. This method utilizes the intensity of the light collected at the excitation wavelength, also referred to as the Rayleigh peak, to probe sample optical properties. Because the Rayleigh peak provides information at only the excitation wavelength, wavelength-dependent variations owing to prominent absorption bands are not corrected. However, for many applications, such as Raman measurements of biological media in the near-infrared (NIR) region, $\mu_a$ and $\mu_s$ are only weakly dependent on wavelength, and thus the method presented here offers a useful measurement. In a preferred embodiment, the Raman excitation wavelength is in a range of 750 nm to 950 nm. This avoids a prominent water absorption peak above 950 nm in blood or tissue, for example.

The following measurements illustrate the effect of turbidity on the Rayleigh peak and an analyte Raman signal. The measurements indicate that the Rayleigh peak is a measure of diffuse reflectance and that Raman intensity and the Rayleigh peak intensity are correlated.

In the following measurements of 49 tissue phantoms in water solutions, following a 7×7 matrix of scattering and absorption properties with ranges similar to that found in biological tissue. The scattering coefficient, $\mu_s$, was varied from 24 to 130 $cm^{-1}$ (median 81.6 $cm^{-1}$) at 830 nm by altering the concentration of Intralipid (Baxter Healthcare), an anisotropic elastic scatterer commonly used to simulate tissue scattering. The absorption coefficient, $\mu_a$, was varied from 0.08 to 1.3 $cm^{-1}$ (median 0.31 $cm^{-1}$) at 830 nm by altering the concentration of India ink (Speedball), which possesses a nearly flat absorption profile in the NIR region. Optical properties of representative tissue phantoms were determined by integrating sphere measurements. A constant 50 mM concentration of creatinine was included in each sample to serve as an indicator of the Raman signal. The relatively high concentration of creatinine enabled higher absorption values to be analyzed while retaining a satisfactory signal-to-noise ratio.

The measurement employed a system such as that illustrated in FIG. 3 with a 830 nm diode laser (Process Instruments) as the excitation source (without using a second broadband source), with power monitored by an external photodiode. The laser was focused through a small hole (4 mm dia.) in an off-axis, gold-coated, half-paraboloidal mirror (Perkin-Elmer) and into a fused silica cuvette (1 cm pathlength) filled with the sample of interest. The laser spot diameter and power at the sample were approximately 1 mm and 250 mW, respectively. Back-scattered Raman and diffusely reflected excitation light were collected with the paraboloidal mirror and sent through a holographic notch filter (Kaiser) to reduce the magnitude of the Rayleigh peak. Specular reflection from the cuvette surface passed through the hole in the paraboloidal mirror and was significantly diminished. The collected light was then focused into a fiber bundle (Romack) that transforms the circular shape of the collected light into a vertical line (~400 mm×26 mm). The exit end of the fiber bundle serves as the entrance slit of a modified f/1.4 spectrometer (Kaiser). The light was dispersed with a holographic grating onto a 1300×340 pixel liquid nitrogen-cooled CCD detector (Princeton Instruments). Care was taken to ensure that the Rayleigh peak from the highest scattering samples did not saturate the detector. Spectra were accumulated with a 2 s integration time, and 10 sequential spectra were collected for each sample. Identical excitation-collection geometry was maintained throughout the measurement by fixing the cuvette position. Samples were replaced via pipette following a water rinse and two rinses of the sample of interest. Data were processed off-line for image curvature correction, summation, and removal of cosmic rays. Spectra from 280-1700 cm$^{-1}$ (850-966 nm) were used in all data analysis.

Figure 12A:
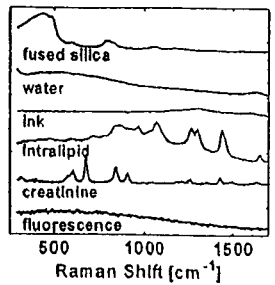
FIGS. 12A and 12B illustrate OLS spectral components and a measured spectrum with the OLS fit and residual, respectively.
Figure 12B:
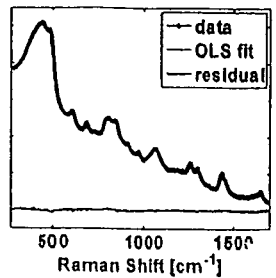

Data were analyzed via ordinary least squares (OLS) using a seven-component model. The model components included fused silica (cuvette), water, Intralipid, India ink, creatinine (as measured in water, with the background subtracted), fluorescence (from impurities in the cuvette—obtained by subtracting the tenth spectrum from the first spectrum for a representative sample), and a DC offset to account for the increased or decreased signal level due to scattering or absorption, respectively. The OLS model components are shown in FIG. 12A. Each spectrum was fit individually to account for varying levels of fluorescence and offset and the creatinine fit coefficients for the 10 spectra in each set were averaged for each sample. A representative spectrum, OLS fit, and residual are shown in FIG. 12B. The residual contains no appreciable structure, supporting the assertion that spectral shape distortions owing to optical property variations over our collected wavelength range are minimal.

The Rayleigh peak was integrated for each spectrum, averaged for each sample, and then normalized to the highest value, which occurred for the sample with highest scattering and lowest absorption. The Rayleigh peak intensity dropped to as low as 20% of the highest value for the sample with lowest scattering and highest absorption. The laser power, however, fluctuated by no more than 0.25% over the course of the experiment. Contributions to the Rayleigh peak from specular reflections are insubstantial with the system used for these measurements. Thus, any variation in the Rayleigh peak intensity can be attributed to sample optical property effects.

Figure 13A:
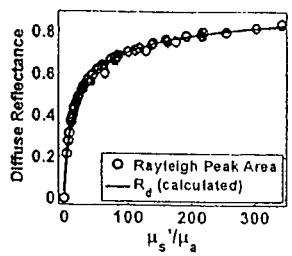
FIGS. 13A and 13B graphically illustrate the Raleigh peak area (open circles) and calculated diffuse reflectance, $R_d$ (solid line) plotted versus the ration $\mu_s'/\mu_a$, and the measured Raman signal, which is linear with respect to the Rayleigh peak area squared, respectively.

With certain collection-excitation geometries diffuse reflectance may be characterized by a single parameter: the ratio $\mu_s'/\mu_a$, where $\mu_s'$ is the transport scattering coefficient, $(1-g)\mu_s$, with g=0.8 for intralipid at the excitation wavelength. A simple exponential model for diffuse reflectance has been derived and shown to be representative of experimentally-obtained diffuse reflectance by Fabbri, et. al. (see Appl. Opt. 42, 3063 (2003) incorporated herein by reference): $R_d = \exp\{-A/[3(1+\mu_s'/\mu_a)]^{1/2}\}$. The A parameter in this expression depends on the refractive index mismatch and the ratio $\mu_s'/\mu_a$. For the experimental work performed by Fabbri, et al., the value of A was set to a constant 7.8, which is for a refractive index mismatch of 1.33. In these measurements, the solutions were contained in a fused silica cuvette with refractive index 1.46. To determine the optimal value for A to fit this function to our Rayleigh peak area data, an iterative procedure based on least-squares fitting was employed. Because this measures relative and not absolute reflectance values, the normalization factor for the Rayleigh peak area data was also determined by the iterative process. The values for A and the normalization factor were found to be 6 and 0.84, respectively. The normalized data and fit are plotted in FIG. 13A versus $\mu_s/\mu_a$. The agreement between the data and the calculated reflectance is likely due to the large collection area of our paraboloidal mirror. From this, it can be concluded that the Rayleigh peak is a suitable measure of diffuse reflectance at 830 nm.

Figure 13B:
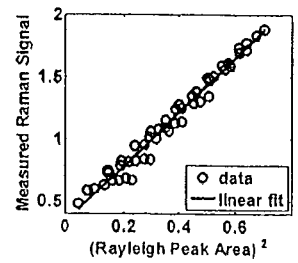

The OLS fit coefficient for creatinine, which serves as the indicator of Raman intensity, is hereafter referred to as the measured Raman signal. In the absence of turbidity, this value should be 1 for all samples, as the concentration of creatinine was constant. However, owing to optical property changes, measured values ranged from 0.48 to 1.88, a deviation of over 140%. The measured Raman signal is also a function of the ratio $\mu_s'/\mu_a$, but with a minor additional dependence on $\mu_a$. The data reveal a quadratic relationship between the measured Raman signal and the Rayleigh peak area (FIG. 13B). This relationship can be used to correct the variations in Raman intensity. The raw Raman spectra were each divided by its Rayleigh peak area scaled according to the quadratic fit of FIG. 13B. The spectra were again fit with the OLS model components to extract the corrected Raman signal (creatinine fit coefficients).

Figure 14A:
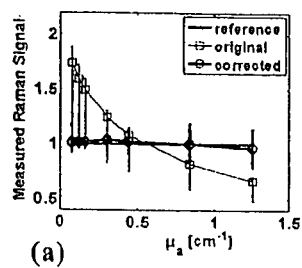
FIGS. 14A and 14B graphically illustrate the measured Raman signal as a function of $\mu_a$ and $\mu_s$, respectively, before (squares) and after (circles) correction. The symbol marks the median value of the Raman signal for the opposing optical property and the bar extends to the maximum and minimum of the optical range.
Figure 14B:
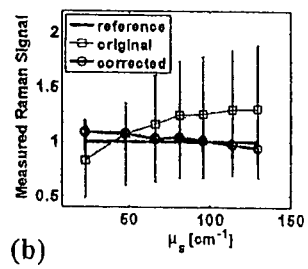

The Raman signal for each of the 49 samples is displayed as a function of $\mu_a$ (FIG. 14A) and $\mu_s$ (FIG. 14B), before and after correction. Symbols are used to depict the median value of the Raman signal for the opposing optical property, and the bars extend across the optical property range. Note that the corrected Raman signal is nearly 1 for all samples, regardless of the optical property variations, indicating that sampling volume variations have been rectified. As a result, the prediction accuracy is significantly improved, with the root mean standard error of prediction (RMSEP) for the uncorrected data at 41.5% versus an RMSEP for the corrected data at 7%.

These measurements indicate that information at the excitation wavelength can be effectively used to correct turbidity-induced intensity distortions in Raman spectra and significantly improve prediction accuracies. The success of this method is, however, dependent on $\mu_a$ and $\mu_s$ being relatively constant over the collected wavelength range. In this case, intensity distortions from sampling volume variations outweigh spectral shape distortions. In cases where spectral distortions are comparable to or greater than intensity distortions, such as in the presence of narrow absorption features, a full spectral range correction using an additional broadband source may offer improved results.

Multivariate calibration is an analytical technique for extracting analyte concentrations in complex chemical systems that exhibit linear response. Multivariate techniques are particularly well suited to analysis of spectral data because information about all of the analytes can be collected simultaneously at many wavelengths.

Explicit and implicit multivariate calibration methods have their own advantages and limitations. Explicit calibration methods are often used when all of the constituent spectra can be individually measured or pre-calculated. Examples are ordinary least squares (OLS) and classical least squares (CLS). Explicit methods provide transparent models with easily interpretable results. However, highly controlled experimental conditions, high quality spectra, and accurate concentration measurements of each of the constituent analytes (or equivalent information) may be difficult to obtain, particularly in biomedical applications.

When all of the individual constituent spectra are not known, implicit calibration methods are often adopted. Principal component regression (PCR) and partial least squares (PLS) are two frequently used methods in this category. Implicit methods require only high quality calibration spectra and accurate concentration measurements of the analyte of interest—the calibration data—greatly facilitating system design. However, unlike explicit methods, the performance of implicit methods cannot be simply judged by conventional statistical measures such as goodness of fit. Spurious effects such as system drift and co-variations among constituents can be incorrectly interpreted as legitimate correlations. Furthermore, implicit methods such as PCR and PLS lack the ability to incorporate additional information beyond the calibration data about the system or analytes. Such prior information has the potential to improve implicit calibration and limit spurious correlations.

The incorporation of prior information into models has been extensively pursued in fields such as pattern recognition, machine learning and inverse problems. The use of prior information generally helps stabilize and enhance deconvolution, classification and/or inversion algorithms. In multivariate calibration, methods combining explicit and implicit schemes have been explored. Owing to prior information about model constituent(s), measurement error variance, or the analyte of interest, these methods in principle outperform those without prior information. However, depending on how prior information is incorporated, these methods may lack robustness due to inaccuracy in the prior information, especially for methods incorporating known analyte spectra, such as hybrid linear analysis (HLA).

HLA utilizes a separately measured spectrum of the analyte of interest together with the calibration data and outperforms methods without prior information such as PLS. However, because HLA relies on the subtraction of the analyte spectrum from the calibration data, it is highly sensitive to the accuracy of the spectral shape and its intensity. For complex turbid samples in which absorption and scattering are likely to alter the analyte spectral features in unknown ways, the performance of HLA is impaired. To provide transcutaneous measurement of blood analytes in vivo, a method has been employed that is more robust against inaccuracies in the previously measured pure analyte spectra.

A preferred embodiment of the present invention employs a method that uses prior spectral information with calibration data in an implicit calibration scheme. Starting with the inverse mixture model as the forward problem, define the inverse problem with solution b. Instabilities associated with the inversion process are removed by means of a technique known as regularization, and prior information is included by means of a spectral constraint. This method is defined as constrained regularization (CR). The effectiveness of CR using numerical simulations is demonstrated using measured Raman spectra. With CR, the standard error of prediction (SEP) is lower than methods without prior information, such as PLS, and is less affected by analyte co-variations. Also, CR is more robust than previously developed hybrid method, HLA, when there are inaccuracies in the applied constraint, as often occurs in complex or turbid samples such as biological tissues. Note that the terms prior information and spectral constraints are used interchangeably for both CR and HLA hereinafter.

Multivariate calibration can be viewed as an inverse problem. Regularization methods, also known as ridge regression in the statistical literature, are mostly used on ill-conditioned inverse problems such as tomographic imaging, inverse scattering and image restoration. These methods seek to obtain a source distribution in the presence of noisy (system-corrupted) data. In the present system, the noise is treated as uncorrelated, which simplifies the analysis.

Implicit calibration schemes require a set of calibration spectra, S, with each spectrum occupying a column of S, associated with several known concentrations of the analyte of interest that are expressed as a column vector, c, the $j^{th}$ element of which corresponds to the $j^{th}$ column of S. Developing an accurate regression vector, b, requires accurate values of c and S. The forward problem for our calibration method is defined by the linear inverse mixture model for a single analyte:

$$c = S^T b. \quad (2)$$

The goal of the calibration procedure is to use the set of data [S,c] to obtain an accurate b by inverting Eq. (2). The resulting b can then be used in Eq. (1) to predict the analyte concentration, C, of an independent prospective sample by measuring its spectrum, s. The "accuracy" of b is usually judged by its ability to correctly predict concentrations prospectively via Eq. (1).

There are two primary difficulties in directly inverting Eq. (2). First, the system is usually underdetermined, i.e., there are more variables (e.g., wavelengths) than equations (e.g., number of calibration samples). Thus, direct inversion does not yield a unique solution. Second, even if a pseudo-inverse exists and results in a unique solution, such a solution tends to be unstable because all measurements contain noise and error. That is, small variations in c or S can lead to large variations in b. Therefore, a more robust solution is required.

The inversion process can be viewed in terms of singular value decomposition (SVD), in which the spectra of the sample set, S, are decomposed into principal component directions, $v_j$, with amplitudes given by their respective singular values, $\sigma_j$. Most of the information in S is captured in the principle components with large $\sigma_j$. The singular values with small amplitudes, although potentially important, are the main cause of instability. Methods to alleviate such instabilities are based on reducing the influence of these small singular values, accomplished by means of a regularization parameter, $\Lambda$. The regularized solution for b is given by:

$$b = \sum_{j=1}^{p} f_j \frac{u_j^T c}{\sigma_j} v_j, \quad (3a)$$

with $$f_j(\Lambda) = \frac{\sigma_j^2}{\sigma_j^2 + \Lambda^2}. \quad (3b)$$

Where $u_j$ and $v_j$ are the eigenvectors of $S^T S$ and $SS^T$, respectively, and p the rank of S. Note that for $\sigma_j \gg \Lambda$, $f_j \approx 1$, and for $\sigma_j \ll \Lambda$, $f_j \approx \sigma_j^2/\Lambda^2$. Thus, one can interpret regularization as providing a smoothing filter $f_j$ that limits the importance of the small singular values. For $\Lambda=0$, Eq. (3) reduces to the least squares solution for b. In PCR, $\Lambda=0$ and only the k largest singular values (k<p) are used. In Wiener filtering, $\Lambda$ is chosen to be the noise-to-signal ratio.

Equation (3) is the regularized solution of Eq. (2), i.e., no prior information is included except by forcing the solution to be finite. However, Eq. (3) can be modified to incorporate prior information. A convenient way to accomplish this is by viewing regularization as the minimization of a quadratic cost function $\Phi$:

$$\Phi(\Lambda, b_0) = \|S^T b - c\|^2 + \Lambda \|b - b_0\|^2, \quad (4)$$

with $\|a\|$ the Euclidean norm (i.e., magnitude) of a, and $b_o$ a spectral constraint that introduces prior information about b. The first term of $\Phi$ is the model approximation error, and the second term is the norm of the difference between the solution and the constraint, which controls the smoothness of the solution and its deviation from the constraint. If $b_o$ is zero, the solution to minimize $\Phi$ is given by Eq. (3). As mentioned above, for $\Lambda=0$ the least squares solution is then obtained. In the other limit, in which $\Lambda$ goes to infinity, the solution is simply $b=b_o$. In the following, a calibration method is selected in which regularization with a properly chosen spectral constraint, $b_o$, is employed, hence the name constrained regularization (CR).

The CR solution, a generalization of Eq. (3), can be analytically derived in SVD form as:

$$b = \sum_{j=1}^{p} \left\{ f_j(\Lambda) \frac{u_j^T c}{\sigma_j} + (1 - f_j(\Lambda)) v_j^T b_0 \right\} v_j. \quad (5)$$

One choice for $b_o$ is the spectrum of the analyte of interest or reference spectrum because that is the solution for b in the absence of noise and interferents. Another choice is the net analyte signal calculated using all of the known pure analyte spectra. Such flexibility in the selection of $b_o$ is owing to the manner in which the constraint is incorporated into the calibration algorithm. For CR, the spectral constraint is included in a nonlinear fashion through minimization of $\Phi$, and is thus termed a "soft" constraint. On the other hand, there is little flexibility for methods such as HLA, in which the spectral constraint is algebraically subtracted from each sample spectrum before performing PCA. This type of constraint can be referred to as a "hard" constraint. CR and HLA are examples showing that the type of constraint affects the robustness of hybrid methods.

Once $b_o$ is chosen, application of CR is straightforward, as Eq. (5) is a direct solution of b and easy to evaluate. A trial value of $\Lambda$ is selected and b is calculated from Eq. (5) using leave-one-out cross validation on the calibration data set to obtain a trial prediction residual error sum of squares (PRESS):

$$PRESS = \Sigma (c_i - \hat{c}_i)^2, \quad (6)$$

where $c_j$ and $\hat{c}_j$ are reference and predicted concentrations, respectively, and i denotes the sample index. $\Lambda$ is then varied until the minimum PRESS value obtained. The resulting value of $\Lambda$ is then used with the full calibration data set, [S,c], to calculate b. This regression vector or transformation can then be used to predict the concentrations of prospective samples with SEP values calculated by the following formula:

$$SEP = \sqrt{\frac{\sum_{i=1}^{n} \|c_i - \hat{c}_i\|^2}{n}}, \quad (7)$$

with n the number of samples in the prospective data set. It is useful to denote the b vector obtained from a particular method herein as $b_{method}$.

Numerical spectra were generated by forming linear combinations of constituent analyte spectra of glucose (G), creatinine (C), and urea (U) as measured in our Raman instrument (FIG. 13). Spectra from 280-1750 $cm^{-1}$ occupying 1051 CCD pixels were binned every 2 adjacent pixels to produce Raman spectra of 525 data points each, reducing the size of the data set for more rapid computation. Random concentrations uniformly distributed between 0 and 10 were used to generate 60 mixture sample spectra, with zero-mean Gaussian white noise generated by MATLAB superimposed on the spectra. The signal-to-noise ratio (SNR), defined here as the ratio of the major Raman peak magnitude to the mean noise magnitude, was ~9. Half of the noise-added spectra formed the calibration set, and the other half the prospective set. Different calibration methods were applied to the calibration set to generate the b vectors by minimizing the respective PRESS through leave-one-out cross validation. The b vectors were then used to calculate the SEP among the prospective set. Repeating this entire procedure, average SEP values and b vectors were obtained for different methods. In all calibrations, no more than 5 factors were needed to obtain optimal prediction in PLS. The pure analyte spectrum of glucose was used as the spectral constraint for CR. Additionally, because all sample-generating constituent analytes were known, OLS was used to establish the best achievable prediction for a given SNR.

Figure 15:
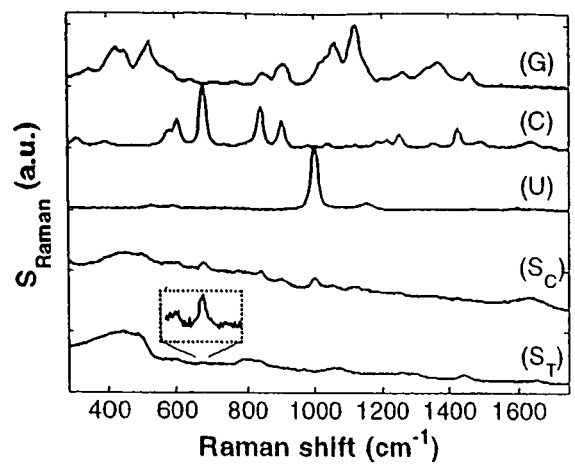
FIG. 15 includes Raman spectra of the ten components used in the simulation: (C): creatinine; (U): urea; (G): glucose; ($S_c$): representative clear sample spectrum and ($S_t$): representative turbid sample spectrum.

In a preferred embodiment, Raman spectra were acquired from 44 water-dissolved mixture samples composed of glucose, creatinine, and urea, each with randomized concentration profiles from 0 to 50 mM, with respective mean ~25 mM. 22 samples were used for the calibration set and the other 22 for the prospective set. Each sample was mixed from stock solutions within 3 minutes of its spectrum being taken. All samples were measured in a 1-cm pathlength quartz cuvette using a Raman instrument. Each spectrum was acquired in 2 s with laser power equivalent to ~30 $mW/mm^2$ and a 1 $mm^2$ spot size at the sample. 30 spectra of each water-dissolved analyte and of water were acquired and averaged for better SNR. Pure analyte spectra were obtained by subtracting the water and quartz spectra from the water-dissolved analyte spectra. A representative sample spectrum (Sc) is displayed in FIG. 15 b vectors obtained using different calibration methods were applied to the prospective set to calculate SEP. In all calibrations, no more than 5 factors were needed to obtain optimal predictions in both PLS and HLA. The pure analyte spectrum of glucose was used as the spectral constraint for both CR and HLA. Because of measurement errors in the pure analyte concentrations (estimated at 1%), as well as to fully exploit HLA, we allowed the amplitude of the pure analyte spectra to vary within 10%.

In another preferred embodiment, the same protocol was followed, but with turbid samples. Raman spectra were acquired from 54 water-dissolved mixture samples composed of glucose, creatinine, India ink, and intralipid with a randomized concentration profile. Analyte concentrations were varied between 5 and 30 mM with mean ~16 mM. The concentration of India ink was varied such that the sample absorption coefficients ranged from 0.1 to 0.2 cm$^{-1}$ with mean ~0.15 cm$^{-1}$. The concentration of intralipid was varied such that the sample scattering coefficients ranged from 35 to 75 cm$^{-1}$ with mean ~55 cm$^{-1}$. The range of optical property changes agree well with reported values measured from human skin. 27 samples were used for the calibration set and the other 27 for the prospective set. A representative sample spectrum ($S_T$) is displayed in FIG. 15. In all calibrations, no more than 6 factors were needed to obtain optimal prediction in both PLS and HLA. It should be mentioned that using prediction error (SEP) to compare results from different methods rather than cross validated error can effectively avoid false interpretation based on chance correlations and overfitting.

Figure 16:
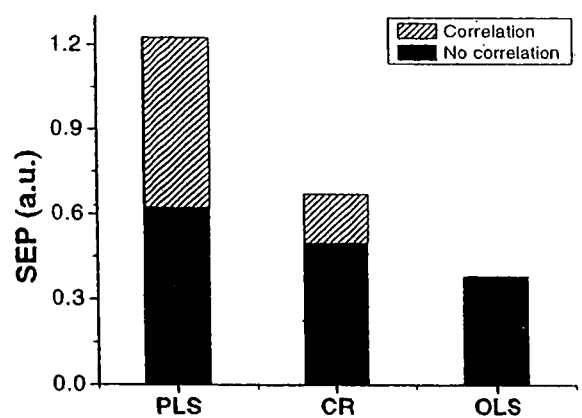
FIG. 16 shows SEP vauves for glucose.
Figure 17A:
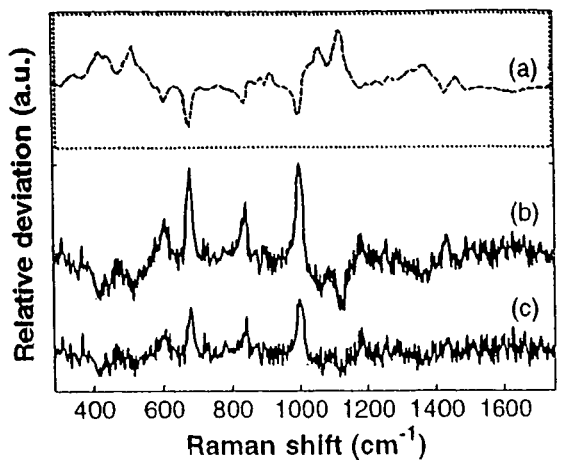
FIG. 17A shows (a) $b_{OLS}$ (b) $b_{PLS}$-$b_{OLS}$ and (c) $b_{CR}$-$b_{OLS}$.

Two numerical methods of analysis were performed on spectra generated from measured constituent analyte spectra, with glucose as the analyte of interest. The first analysis demonstrates that CR significantly outperforms PLS when all analyte concentrations vary in a random fashion. The results, summarized in FIG. 16 (solid bars), show that with the aid of prior information, CR generates lower SEP values than PLS. The reason for this is visualized in FIG. 17A, in which the deviation of $b_{PLS}$ and $b_{CR}$ from the ideal $b_{OLS}$ is plotted. Note that $b_{CR}$ better converges to $b_{OLS}$, therefore improving prediction over PLS.

The second simulation demonstrates that CR is less susceptible to spurious correlations among covarying analytes. The calibration data set has been modified such that the concentration of the analyte of interest correlates to another analyte with $R^2$~0.5. The prospective set remained uncorrelated. The results are displayed in FIG. 16, with the hatched bars depicting the increased prediction error when the correlations exist. It is observed that CR is much less affected by analyte correlations than PLS.

Figure 17B:
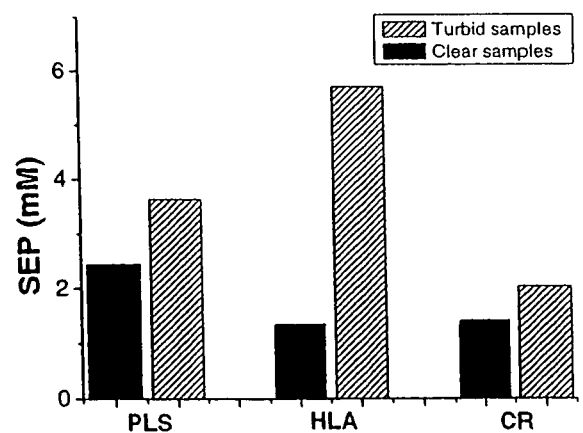
FIG. 17B shows SEP valves for glucose for clear and turbid samples.

SEP values for glucose obtained from PLS, BLA, and CR in the first measurement with clear samples are summarized in FIG. 17B with solid bars. OLS values are not listed because the three constituent model does not account for all measurable variations, e.g. low amounts of fluorescence from the quartz cuvette; therefore, OLS no longer provides the best achievable performance. Among the implicit calibration techniques, substantial improvement over PLS is observed using the hybrid methods. CR and HLA generate similar SEP values, suggesting that these two methods have comparable performance under highly controlled experimental conditions with clear samples.

SEP values obtained from PLS, HLA, and CR in the second experiment with turbid samples are summarized in FIG. 17B with hatched bars. Substantial improvement over both PLS and HLA is observed using CR. The performance of HLA is significantly impaired as a result of the turbidity induced intensity variations of the analyte of interest. In HLA, the analyte of interest is assumed to be present in the data according to the reference concentrations. This assumption leads to the first and most important step: the removal of the spectral contribution of the analyte of interest from the data by subtracting the known spectrum of the analyte according to its concentration in each sample. As a result, the performance in HLA depends on the "accuracy" of the constraint, as well as the legitimacy of the assumption. In CR, however, the constraint only guides the inversion, allowing the minimization algorithm to arrive at the optimal solution, thereby reducing its dependency on the accuracy of the constraint. Further, unlike HLA, which models the residual data after removing the analyte contribution, CR retains data fidelity and is unlikely to produce false built-in analyte spectral features in the b vector.

The results demonstrate that there is a tradeoff between maximizing prior information utilization and robustness concerning the accuracy of such information. Multivariate calibration methods range from explicit methods with maximum use of prior information (e.g. OLS, least robust), hybrid methods with a hard constraint (e.g. HLA), hybrid methods with a soft constraint (e.g. CR), and implicit methods with no prior information (e.g. PLS, most robust). CR achieves a preferred balance between these ideals for practical situations.

Constrained regularization is a hybrid method for multivariate calibration. Strictly speaking, it should be categorized as an implicit calibration method with one additional piece of information, the spectrum of the analyte of interest. In the broader context, regularization methods may perform somewhat better than either PLS or PCR for certain data structures. A heuristic explanation is that regularization provides a continuous "knob", and therefore can be used to find a better balance between model complexity and noise rejection. These results show that in addition to this plausible intrinsic advantage, an improvement can be obtained by incorporating a solution constraint.

CR significantly outperforms methods without prior information such as PLS and is less susceptible to spurious correlations with co-varying analytes. Compared to HLA, CR has superior robustness with less accurate spectral constraints. This robustness is crucial for hybrid methods because it is difficult, if not impossible, to quantify high-fidelity pure analyte spectra in complex systems such as biological tissues. Further, CR naturally extends to situations in which pure spectra of more than one constituent are also known. In that case a better choice of constraint ($b_o$) might be the net analyte signal calculated from all the known pure spectra. CR is thus able to include more prior information without sacrificing the principal advantage of implicit calibration: that only the reference concentrations of the analytes of interest are required in addition to the calibration spectra.

Figure 18A:
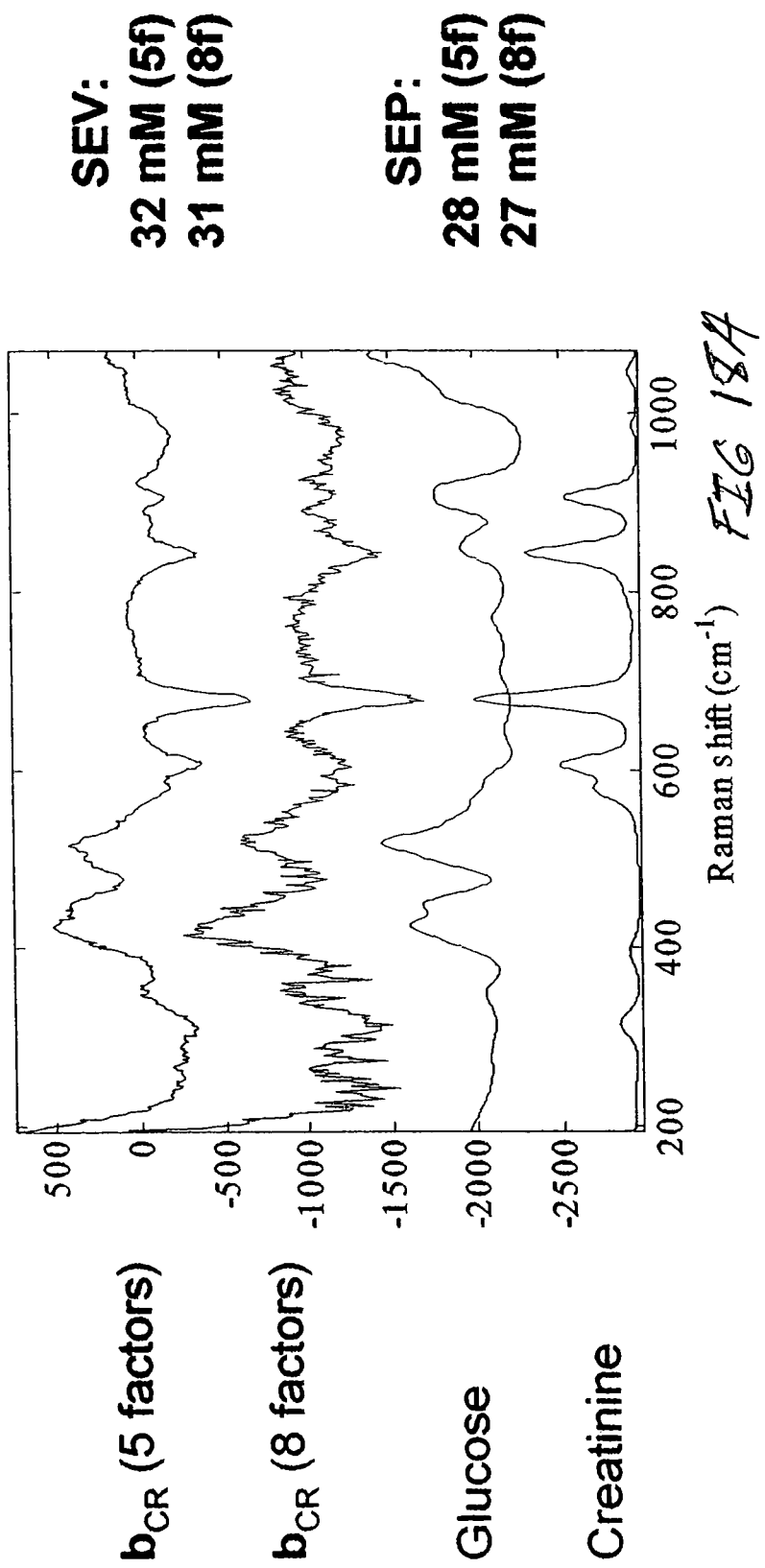
FIG. 18A shows a plot for corrected Raman data.

FIG. 18A shows a combination of constrained regularization (CR) and (IRS) corrected Raman spectra. The regression vector DCR is used to generate spectra along with IRS spectra to provide improved calibrated measurements. FIG. 18B illustrates a method of employing constrained regularization to calibrate a spectrum.

While the present invention has been described herein in conjunction with a preferred embodiment, a person with ordinary skill in the art, after reading the foregoing specification, can effect changes, substitutions of equivalents and other types of alterations to the systems and methods that are set forth herein. Each embodiment described above can also have included or incorporated therewith such variations as disclosed in regard to any or all of the other embodiments. Thus, it is intended that protection granted by Letters Patent herein be limited in breadth only by the appended claims and any equivalents thereof.

What is claimed:

1. A system for measurement of a blood analyte comprising:
    a first light source that emits Raman excitation light;
    a second light source;
    a probe having a fiber optic light delivery and collection system for coupling the first light source and the second light source onto a region of material having an endogenous blood analyte, the system collecting Raman light and reflected light returning from the region of material;
    a detector optically coupled to a proximal end of the probe that detects the collected Raman light and reflected light and generates Raman data and reflected light data; and a processing system connected to the detector such that the processing system receives the Raman data and the reflected light data, the processing system processing the Raman data, reflected light data and a reference Raman spectrum of one or more blood analytes to provide spectral data indicating a concentration of the endogenous blood analyte in the region of material.

2. The system of claim 1 wherein the detector detects a diffuse reflectance spectrum and the processing system determines a sampling volume within a subject.

3. The system of claim 1 wherein the first light source comprises a laser that emits at a wavelength in a range of 750 nm to 1200 nm.

4. The system of claim 1 wherein the probe is coupled to a spectrograph.

5. The system of claim 1 wherein the processing system determines a ratio of Raman data and diffuse reflectance data to provide corrected spectral data.

6. The system of claim 1 wherein the second light source emits broadband light that is coupled to the optical delivery system.

7. The system of claim 1 wherein the first light source comprises an infrared laser.

8. The system of claim 1 wherein the first light source emits in a range of 750 nm to 1200 nm.

9. The system of claim 1 wherein the fiber optic probe is coupled to a fiber optic coupler.

10. The system of claim 9 wherein system comprises a first fiber optic cable optically coupled to the first light source and a second fiber optic cable optically coupled to the second light source, a combiner optically coupling the first fiber optic cable and the second fiber optic cable to the probe fiber optic cable.

11. The system of claim 1 wherein the detector measures a reflectance spectrum including light reflected by the material at a Raman excitation wavelength that is emitted by the first light source.

12. The system of claim 11 wherein the Raman excitation wavelength is in a range of 750 nm to 950 nm.

13. The system of claim 11 wherein the detector measures a Raman spectrum in response to the Raman excitation wavelength.

14. The system of claim 11 further comprising a processor that processes collected Raman data and collected reflected light data generated by the detector.

15. The system of claim 14 further comprising the processor is adapted to condition the Raman data with the reflected light data.

16. The system of claim 15 wherein the processor determines an area of a reflected light spectrum about a Raman excitation wavelength.

17. The system of claim 16 wherein the processor conditions the Raman data with said area.

18. The system of claim 17 wherein the processor divides a Raman spectrum with said area.

19. The system of claim 14 wherein the processor processes the Raman data to correct for measurement volume variations in a plurality of Raman data measurements.

20. The system of claim 1 further comprising a processor connected to detector that applies a transformation to a detected spectrum to determine a blood analyte concentration.

21. The system of claim 20 further comprising the processor is adapted to define the transformation as a function including a spectral constraint.

22. The system of claim 21 wherein the spectral constraint comprises a spectrum of the analyte.

23. The system of claim 22 wherein the analyte spectrum comprises a spectrum of glucose.

24. The system of claim 21 wherein the spectral constraint comprises a plurality of spectra of different analytes.

25. The system of claim 21 wherein the processor determines a minimized function to define the transformation.

26. The system of claim 20, wherein the processor processes the detected Raman spectrum and a detected reflectance spectrum in combination with the transformation to provide a corrected spectrum.

27. The system of claim 26 wherein the transformation comprises a spectral constraint.

28. The system of claim 1 further comprising a calibration phantom.

29. The system of claim 1 further comprising the probe has a light delivery fiber and a plurality of light collection optical fibers.

30. The system of claim 29 wherein the probe collects light returning from a region of skin of a subject.

31. The system of claim 30 further comprising a reflector that couples the returning light into a plurality of collection fibers.

32. The system of claim 31 wherein the probe couples the returning light to a spectrograph, the spectrograph coupling dispersed light to the detector.

33. The system of claim 29 wherein the probe has a distal filter.

34. The system of claim 1 further comprising a second detector that monitors light source output.

35. The system of claim 1 further comprising a controller that actuates the first light source.

36. The system of claim 35 wherein the controller actuates a shutter device.

37. The system of claim 1 wherein the includes a light path with a reflector.

38. The system of claim 1 wherein the second light source comprises a white light source that is coupled to the material for a reflectance measurement.

39. The system of claim 1 further comprising a container that contains a sample of material removed from a body to be measured by the system.

40. A method of measuring a blood analyte comprising:
illuminating a material with light from a first light source and a second light source;
detecting a Raman spectrum and a reflectance spectrum from the material in response to the illuminating light; and
processing the detected Raman spectrum and the reflectance spectrum to provide a processed spectrum to measure an endogenous blood analyte within the material, the processing step including calculating a regularized spectrum using a reference Raman spectrum of one or more blood analytes.

41. The method of claim 40 further comprising determining a concentration of an analyte with the processed spectrum.

42. The method of claim 40 further comprising illuminating a sample with a laser excitation wavelength and detecting the reflected light spectrum and the Raman spectrum in response.

43. The method of claim 40 further comprising illuminating a sample with a first narrowband light source to measure the Raman spectrum and a broadband light source to measure the reflectance spectrum.

44. The method of claim 40 further comprising storing a plurality of reference spectra in a memory, each reference spectrum corresponding to a separate blood analyte.

45. The method of claim 44 wherein the analytes comprise glucose, creatinine and urea.

46. The method of claim 40 further comprising delivering and a collecting light using a fiber optic probe.

47. The method of claim 46 further comprising collecting Raman light with a first plurality of collection fibers and collecting reflected light with a second plurality of collection fibers.

48. A system for measurement of a blood analyte comprising:
   a first light source that emits a Raman excitation light;
   a second light source;
   an optical delivery system for coupling the first light source and the second light source through skin of a subject onto a region of material having an endogenous blood analyte;
   an optical collection system that collects Raman and reflected light returning from the region in response to the Raman excitation light and light incident on the region from the second light source;
   a detector that detects the collected Raman and reflected light to generate Raman data and reflected light data; and
   a processing system connected to the detector such that the processing system processes the Raman data, the reflected light data and a reference Raman spectrum of one or more blood analytes to measure the endogenous blood analyte.

49. The system of claim 48 wherein the processing system processes the Raman data and reflected light data to provide spectral data indicating a concentration of analyte in the region of material.

50. The system of claim 49 wherein the processing system determines a ratio of Raman data and diffuse reflectance data to provide corrected spectral data.

51. The system of claim 48 wherein the detector detects a diffuse reflectance spectrum and the processing system determines a sampling volume within a subject.

52. The system of claim 48 wherein the first light source comprises a laser that emits at a wavelength in a range of 750 nm to 1200 nm.

53. The system of claim 48 wherein the optical collection system comprises a fiber optic coupler and a spectrograph.

54. The system of claim 48 wherein the first light source emits a single narrowband light signal to induce a Raman light emission and a reflected light emission that are detected by the detector.

55. The system of claim 54 wherein the detector detects the reflected light emission over a range of wavelengths of the narrowband light signal.

56. The system of claim 48 wherein the first light source comprises a laser.

57. The system of claim 48 wherein the first light source emits in a range of 750 nm to 1200 nm.

58. The system of claim 48 wherein the optical delivery system comprises a fiber optic delivery system.

59. The system of claim 48 wherein the detector measures a reflectance spectrum including light reflected by the material at a Raman excitation wavelength that is emitted by the first light source.

60. The system of claim 59 wherein the Raman excitation wavelength is in a range of 750 nm to 950 nm.

61. The system of claim 48 wherein the processing system processes collected Raman data and collected reflected light data generated by the detector to determine a glucose concentration.

62. The system of claim 61 wherein the processing system determines an area of a reflected light spectrum about a Raman excitation wavelength.

63. The system of claim 61 wherein the processing system processes the Raman data to correct for measurement volume variations in a plurality of Raman data measurements.

64. The system of claim 48 wherein the processing system processes the Raman data with the area of a reflected light spectrum.

65. The system of claim 64 wherein the processing system divides a Raman spectrum with said area.

66. The system of claim 48 wherein the processing system applies a transformation to a detected spectrum to determine an analyte concentration.

67. The system of claim 66 wherein the processing system applies the transformation as a function including a spectral constraint.

68. The system of claim 67 wherein the spectral constraint comprises a spectrum of the analyte.

69. The system of claim 68 wherein the analyte spectrum comprises a spectrum of glucose.

70. The system of claim 48 wherein the collected reflected light has a spectrum in a range of 750 nm to 950 nm.

* * * * *